United States Patent
Ham et al.

(10) Patent No.: US 11,717,474 B2
(45) Date of Patent: Aug. 8, 2023

(54) METHOD OF CONTINUOUSLY PRODUCING CANNABINOL FROM CANNABIS PLANT AND USES THEREOF

(71) Applicant: KOREA INSTITUTE OF SCIENCE AND TECHNOLOGY, Seoul (KR)

(72) Inventors: Jungyeob Ham, Gangneung-si (KR); Taejung Kim, Gangneung-si (KR); Bong Chul Chung, Seoul (KR); Sungdo Ha, Gangneung-si (KR); Seok Lee, Seoul (KR); Jin-Chul Kim, Gangneung-si (KR); Pilju Choi, Gangneung-si (KR); Bong Geun Song, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 228 days.

(21) Appl. No.: 17/138,312

(22) Filed: Dec. 30, 2020

(65) Prior Publication Data
US 2021/0196608 A1    Jul. 1, 2021

(51) Int. Cl.
| | |
|---|---|
| *A61K 36/00* | (2006.01) |
| *A61K 8/49* | (2006.01) |
| *C07D 311/80* | (2006.01) |
| *A23L 33/105* | (2016.01) |
| *A23L 5/30* | (2016.01) |

(52) U.S. Cl.
CPC ............. *A61K 8/498* (2013.01); *A23L 5/34* (2016.08); *A23L 33/105* (2016.08); *C07D 311/80* (2013.01); *A23V 2002/00* (2013.01); *A61K 2236/333* (2013.01); *A61K 2236/37* (2013.01)

(58) Field of Classification Search
CPC ........................................................ A23L 5/34
See application file for complete search history.

(56) References Cited

U.S. PATENT DOCUMENTS

| | | | |
|---|---|---|---|
| 2008/0221339 A1* | 9/2008 | Webster | ............... C07D 311/80 549/390 |
| 2019/0038663 A1 | 2/2019 | Kotra et al. | |
| 2019/0160393 A1 | 5/2019 | Marshall et al. | |

FOREIGN PATENT DOCUMENTS

| | | | | |
|---|---|---|---|---|
| WO | WO-2018102711 A1 * | 6/2018 | ........... | A61K 36/185 |
| WO | WO 2019/100172 A1 | 5/2019 | | |
| WO | WO 2019/211795 A1 | 11/2019 | | |
| WO | WO-2019211794 A1 * | 11/2019 | | |

OTHER PUBLICATIONS

Chang et al., "Microwave-Assisted Extraction of Cannabinoids in Hemp Nut Using Response Surface Methodology: Optimization and Comprehensive Study," Molecules (2017), vol. 22, pp. 1-15.
Office Action dated Jun. 21, 2021, in Republic of Korea Patent Application No. 10-2019-0179810.

* cited by examiner

*Primary Examiner* — Qiuwen Mi
(74) *Attorney, Agent, or Firm* — Birch, Stewart, Kolasch & Birch, LLP

(57) ABSTRACT

Provided are: a method of preparing a cannabis processed product having an increased CBN content in an efficient and economic manner, through cyclization of CBD and aromatization of THC by continuous microwave irradiation of a cannabis extract; and use of a processed product having an increased CBN content prepared by the method, a fraction thereof, and a single ingredient of CBN, in foods, drugs, and cosmetics.

17 Claims, 36 Drawing Sheets

METHOD OF CONTINUOUSLY PRODUCING CANNABINOL FROM CANNABIS PLANT AND USES THEREOF

CROSS-REFERENCE TO RELATED APPLICATION

This application is based on and claims priority under 35 U.S.C. § 119 to Korean Patent Application No. 10-2019-0179810, filed on Dec. 31, 2019, in the Korean Intellectual Property Office, the disclosure of which is incorporated by reference herein in its entirety.

BACKGROUND

1. Field

The present disclosure relates to a continuous preparation method for increasing the cannabinol (CBN) content from *Cannabis sativa* L. and an extract thereof using microwaves, and use thereof.

2. Description of Related Art

Cannabis (*Cannabis sativa* L.) is an annual plant belonging to the genus *Cannabis* in the family Cannabaceae, which has been widely cultivated in temperate and tropical areas, mainly in Central Asia, for 12,000 years, and includes wild-type cannabis, and collectively refers to cannabis chemovars, which contain different kinds of cannabinoid compounds known as medical/pharmaceutical ingredients, and variants thereof, *Cannabis sativa* subspecies *sativa* including variants var. *indica* and var. *kafiristanica*, *Cannabis sativa* subspecies *indica*, *Cannabis sativa* subspecies *ruderalis*, and plants which are the result of genetic crosses, self-crosses, or hybrids thereof.

According to Korean and Chinese traditional medical records, mazain (麻子仁) or hwamain (火麻仁), which is a peeled seed of cannabis, has been used for constipation, diabetes, pain diseases, menstrual disorders, skin diseases, dysentery, etc., and cannabis weed which is a cannabis leaf has been used for anthelmintic, hair protection, asthma, analgesic, anesthetic, diuretic purposes, etc. Further, cannabis root has been used to treat difficult births and to relieve blood stasis, cannabis skin has been used for bruises, irritating rashes and distending pain, cannabis flower has been used for paralysis, itching, etc., and cannabis flower neck has been used for difficult births, constipation, gout, insanity, insomnia, etc. There are records that each part of cannabis were appropriately used according to the condition.

Cannabis includes about 400 compounds, and most of them are cannabinoids, terpenes, and phenolic compounds. There are about 90 kinds of cannabinoids, which are medically/pharmacologically important natural ingredients, and there are many ingredients found only in cannabis.

Among the cannabinoids of cannabis, a psychotropic ingredient is $\Delta^9$-tetrahydrocannabinol ($\Delta^9$-THC), and cannabidiol (CBD), which is a non-psychotropic ingredient, is known to exhibit physiologically active effects through various receptors in the human body, including adrenergic receptors and cannabinoid receptors.

In particular, while scientists were studying the mechanism of psychotropic action of cannabis, in 1988, they discovered a receptor in the brain to which cannabinoid selectively binds, indicating that molecules similar to cannabinoids are also produced in the body. These cannabinoid molecules are fatty acid-type neurotransmitters locally produced in the brain, and also called anandamide. Currently known cannabis receptors are divided into two types. CB1 receptors are distributed throughout the brain, including in the cerebral cortex, hippocampus, cerebellum, basal ganglia, etc. CB2 receptors are mainly distributed in macrophages or peripheral tissues such as bone marrow, lungs, pancreas, smooth muscle, etc., and are closely related to the immune system.

$\Delta^9$-THC is a main active ingredient of cannabis used for medicinal purposes. $\Delta^9$-THC is an agonist with a strong affinity for CB1 receptors, and is known to exhibit a main mechanism of psychotropic action. Many experimental results have revealed that CBD has beneficial effects such as anti-inflammatory action, antiepileptic action, antiemetic action, anti-cancer action, etc. Further, CBD reduces the negative effects of $\Delta^9$-THC, and inhibits reuptake and breakdown of anandamide, which is an endogenous cannabinoid, through antagonistic action on CB1 and CB2 receptor agonists such as $\Delta^9$-THC, and is also known as a serotonin receptor agonist. It was also revealed that cannabichromene, which is an ingredient of cannabis, has anti-inflammatory, sedative, antifungal actions, etc., and cannabinol (CBN) helps boost immune function by binding to CB2 receptors rather than CB1 receptors, and also has anti-inflammatory, pain relief, sleep induction, appetite enhancing, and anticonvulsant effects. Much research has been very actively conducted on pharmacological mechanisms of ingredients included in cannabis.

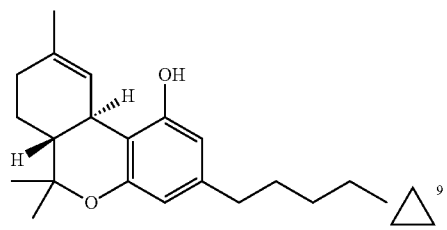

Tetrahydrocannabinol, $\Delta^9$-THC

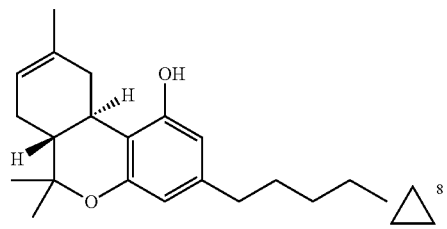

Tetrahydrocannabinol, $\Delta^8$-THC

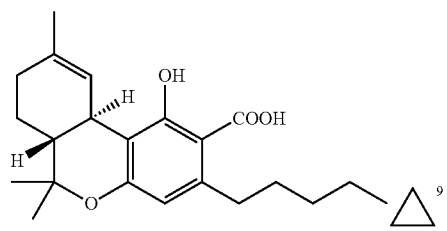

Tetrahydrocannabinolic acid, Δ⁹-THCA

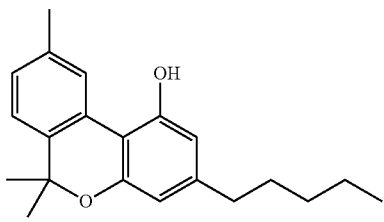 [SMILES: CCCCCc1cc(O)c2c(c1)OC(C)(C)c1ccc(C)cc1-2]

Cannabinol, CBN

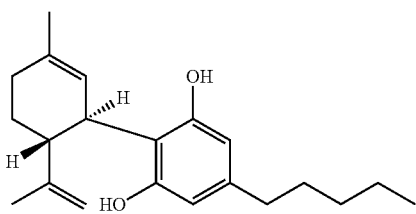 [SMILES: C=C(C)[C@@H]1CCC(C)=C[C@H]1c1c(O)cc(CCCCC)cc1O]

Cannabidiol, CBD

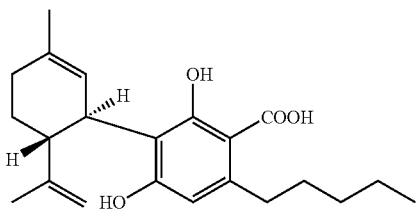 [SMILES: C=C(C)[C@@H]1CCC(C)=C[C@H]1c1c(O)cc(CCCCC)c(C(=O)O)c1O]

Cannabidiolic acid, CBDA

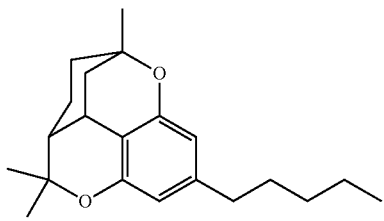 [SMILES: CCCCCc1cc2c3c(c1)OC(C)(C)C1CCC(C)(CC31)O2]

Cannabicitran

Dronabinol (brand name: Marinol) and nabilone (brand name: Cesamet), which are oral forms of Δ⁹-THC approved by the US Food and Drug Administration (FDA), are being sold as relievers for chemotherapy-induced side-effects and as appetite stimulants for AIDS patients, and extensive studies have been actively conducted on active ingredients of cannabis, such as clinical trials for Epidiolex which is a liquid drug including CBD as a main ingredient for children with epilepsy, Resunab which is a CB2 receptor-binding synthetic cannabinoid formulation for the treatment of systemic lupus erythematosus, and Cannador (Δ⁹-THC: CBD=2:1) which is not a single Δ⁹-THC or CBD drug but in the form of a cannabis extract for the treatment of multiple sclerosis and severe chronic pain disorders, etc.

Accordingly, the present inventors have developed technologies for changing the contents of main pharmaceutical ingredients of cannabis using microwave processing technology that has been accumulated so far, and as a result, have found that CBD and Δ⁹-THC are easily converted into CBN through a microwave cyclization or aromatization while continuously applying a reaction mixture, thereby completing the present disclosure.

SUMMARY

An aspect provides a method of continuously producing cannabinoids, the method including irradiating microwaves to a reaction mixture including a sample including one or more of CBD and THC, an acid, and a solvent in a reaction vessel, wherein the microwave irradiation is carried out by flowing the reaction mixture from an inlet of the reaction vessel and out through an outlet of the reaction vessel.

Another aspect provides a method of continuously producing cannabinoids, the method including irradiating microwaves to a reaction mixture including Cannabis sp. plant or an extract thereof, and a solvent in a reaction vessel, wherein the microwave irradiation is carried out by flowing the reaction mixture from an inlet of the reaction vessel and out through an outlet of the reaction vessel.

Still another aspect provides a composition including cannabinoids produced by the above method.

Still another aspect provides a method of treating a disease of an individual, the method including administering, to the individual, a composition including, as an active ingredient, the cannabinoids isolated by the above method.

Still another aspect provides a cosmetic method, the method including applying, to an individual, a composition including, as an active ingredient, the cannabinoids isolated by the above method.

Additional aspects will be set forth in part in the description which follows and, in part, will be apparent from the description, or may be learned by practice of the presented embodiments of the disclosure.

An aspect provides a method of continuously producing cannabinoids, the method including irradiating microwaves to a reaction mixture including a sample including one or more of CBD and THC, an acid, and a solvent in a reaction vessel, wherein the microwave irradiation is carried out by flowing the reaction mixture from an inlet of the reaction vessel and out through an outlet of the reaction vessel. The method may further include isolating cannabinoid from the microwave-irradiated reaction mixture. The sample including one or more of CBD and THC may be a plant including one or more of CBD and THC, for example, a Cannabis sp. plant or an extract thereof. The sample may include one or more of CBD and THC of 1%, 3%, 5%, 10%, 15%, or 20% or more with respect to the weight of the sample.

Another aspect provides a method of continuously producing cannabinoids, the method including irradiating microwaves to a reaction mixture including a Cannabis sp. plant or an extract thereof and a solvent in a reaction vessel, wherein the microwave irradiation is carried out by flowing the reaction mixture from an inlet of the reaction vessel and out through an outlet of the reaction vessel. The method may further include isolating cannabinoids from the microwave-irradiated reaction mixture.

In the method, the reaction vessel may have a tubular shape and its length in the flow direction of the reaction mixture may be longer than its height. The height may be a length in the direction perpendicular to the flow direction of the reaction mixture. The length in the flow direction may be 0.5 times, 1 time, 2 times, 3 times, 4 times, 5 times, 10 times, 15 times, 50 times, 100 times, 1000 times, 1500 times, 2000 times, 5000 times, 10,000 times, 0.5 times to 10,000 times, 1.0 time to 10,000 times, 5 times to 10,000 times, 10 times to 10,000 times, 100 times to 10,000 times, or 1000 times to 10,000 times the height. The height may be 0.01 cm to 3.0 cm, for example, 0.01 cm to 2.5 cm, 0.01 cm to 2.0 cm, 0.01 cm to 1.5 cm, 0.01 cm to 1.0 cm, 0.01 cm to 0.8 cm, 0.01 cm to 0.6 cm, 0.01 cm to 0.5 cm, 0.02 cm to 3.0 cm, 0.02 cm to 2.5 cm, 0.02 cm to 2.0 cm, 0.02 cm to 1.5 cm, 0.02 cm to 1.0 cm, 0.02 cm to 0.8 cm, 0.02 cm to 0.6 cm, 0.02 cm to 0.5 cm, 0.04 cm to 3.0 cm, 0.04 cm to 2.5 cm, 0.04 cm to 2.0 cm, 0.04 cm to 1.5 cm, 0.04 cm to 1.0 cm, 0.04 cm to 0.8 cm, 0.04 cm to 0.6 cm, 0.04 cm to 0.5 cm, 0.06 cm to 3.0 cm, 0.06 cm to 2.5 cm, 0.06 cm to 2.0 cm, 0.06 cm to 1.5 cm, 0.06 cm to 1.0 cm, 0.06 cm to 0.8 cm, 0.06 cm to 0.6 cm, or 0.06 cm to 0.5 cm. The height may be the inside diameter of the tube. Further, the length in the flow direction may be 1.0 cm to 30,000 cm, for example, 1.0 cm to 25,000 cm, 1.0 cm to 20,000 cm, 1.0 cm to 15,000 cm, 1.0 cm to 10,000 cm, 1.0 cm to 8,000 cm, 1.0 cm to 6,000 cm, 1.0 cm to 4,000 cm, 1.0 cm to 3,000 cm, 100.0 cm to 30,000 cm, 100.0 cm to 25,000 cm, 100.0 cm to 20,000 cm, 100.0 cm to 15,000 cm, 100.0 cm to 10,000 cm, 100.0 cm to 8,000 cm, 100.0 cm to 6,000 cm, 100.0 cm to 4,000 cm, 100.0 cm to 3,000, 500.0 cm to 30,000 cm, 500.0 cm to 25,000, 500.0 cm to 20,000 cm, 500.0 cm to 15,000, 500.0 cm to 10,000, 500.0 cm to 8,000, 500.0 cm to 6,000, 500.0 cm to 4,000, 500.0 cm to 3,000 cm, 1000.0 cm to 30,000 cm, 1000.0 cm to 25,000 cm, 1000.0 cm to 20,000 cm, 1000.0 cm to 15,000 cm, 1000.0 cm to 10,000 cm, 1000.0 cm to 8,000 cm, 1000.0 cm to 6,000 cm, 1000.0 cm to 4,000, or 1000.0 cm to 3,000 cm.

The reaction vessel may have a tubular shape having its length in the flow direction of the reaction mixture and its height, wherein the length may be 1.0 cm to 30,000 cm, for example, 1.0 cm to 25,000 cm, 1.0 cm to 20,000 cm, 1.0 cm to 15,000 cm, 1.0 cm to 10,000 cm, 1.0 cm to 8,000 cm, 1.0 cm to 6,000 cm, 1.0 cm to 4,000 cm, 1.0 cm to 3,000 cm, 100.0 cm to 30,000 cm, 100.0 cm to 25,000 cm, 100.0 cm to 20,000 cm, 100.0 cm to 15,000 cm, 100.0 cm to 10,000 cm, 100.0 cm to 8,000 cm, 100.0 cm to 6,000 cm, 100.0 cm to 4,000 cm, 100.0 cm to 3,000, 500.0 cm to 30,000 cm, 500.0 cm to 25,000, 500.0 cm to 20,000, 500.0 cm to 15,000, 500.0 cm to 10,000, 500.0 cm to 8,000, 500.0 cm to 6,000, 500.0 cm to 4,000, 500.0 cm to 3,000 cm, 1000.0 cm to 30,000 cm, 1000.0 cm to 25,000 cm, 1000.0 cm to 20,000 cm, 1000.0 cm to 15,000 cm, 1000.0 cm to 10,000 cm, 1000.0 cm to 8,000 cm, 1000.0 cm to 6,000 cm, 1000.0 cm to 4,000, or 1000.0 cm to 3,000 cm and the height such as an inner diameter may be 0.01 cm to 3.0 cm, for example, 0.01 cm to 2.5 cm, 0.01 cm to 2.0 cm, 0.01 cm to 1.5 cm, 0.01 cm to 1.0 cm, 0.01 cm to 0.8 cm, 0.01 cm to 0.6 cm, 0.01 cm to 0.5 cm, 0.02 cm to 3.0 cm, 0.02 cm to 2.5 cm, 0.02 cm to 2.0 cm, 0.02 cm to 1.5 cm, 0.02 cm to 1.0 cm, 0.02 cm to 0.8 cm, 0.02 cm to 0.6 cm, 0.02 cm to 0.5 cm, 0.04 cm to 3.0 cm, 0.04 cm to 2.5 cm, 0.04 cm to 2.0 cm, 0.04 cm to 1.5 cm, 0.04 cm to 1.0 cm, 0.04 cm to 0.8 cm, 0.04 cm to 0.6 cm, 0.04 cm to 0.5 cm, 0.06 cm to 3.0 cm, 0.06 cm to 2.5 cm, 0.06 cm to 2.0 cm, 0.06 cm to 1.5 cm, 0.06 cm to 1.0 cm, 0.06 cm to 0.8 cm, 0.06 cm to 0.6 cm, or 0.06 cm to 0.5 cm. The reaction vessel may be at least partially or entirely made of a microwave-transparent or semi-transparent material. The microwave-transparent material refers to a material that passes a substantial portion of microwave energy irradiated from a microwave generator and allows it to reach the inside of the reaction vessel. The microwave-transparent material may be, for example, thermoplastics, glass, or a combination thereof. The microwave-transparent material may be Teflon such as glass-filled Teflon, polytetrafluoroethylene (PTFE), and perfluoroalkoxy alkanes (PFA), poly(methyl methacrylate) (PMMA), polyetherimide (PEI), aluminum oxide, glass, or a combination thereof.

The reaction vessel may include an inlet and an outlet to which a channel is connected, the channel through which a fluid may flow, and a pump capable of applying a pressure to the fluid and a pressure regulator such as a back pressure regulator may be connected to the channel, respectively. The pressure regulator may be a back pressure regulator. The reaction vessel may be connected to a temperature controller for controlling the temperature inside the reaction vessel. The temperature controller may be a chamber including the reaction vessel and may include a liquid medium. In irradiating microwaves to the reaction mixture included in the reaction vessel, when the microwave is required to pass through the chamber including the reaction vessel, the chamber material may include the microwave-transparent material. The chamber may have any shape as long as it includes the reaction vessel, for example, a long pipe or tube.

The liquid medium is a liquid medium capable of transferring heat to the reaction vessel. The liquid medium may be the same as the solvent in the reaction mixture. In addition, the liquid medium may be water, C5-C10 alcohol, C2-C6 diol, C3-C6 triol, a polymer thereof, or a mixture thereof.

Since the inlet of the reaction vessel is connected to a channel through which a fluid may flow, the sample or solvent may be continuously introduced. Accordingly, one or more of $\Delta^8$-THC, $\Delta^9$-THC, and CBN may be continuously produced by continuously flowing the reaction mixture from the inlet and out through the outlet and irradiating microwaves during flowing.

Therefore, the reaction vessel may be connected to the temperature controller. The reaction vessel may be connected by flowing through the temperature controller, and the temperature controller may include a temperature control chamber capable of containing a liquid. The temperature control chamber material may include a microwave-transparent material. The temperature control chamber material may have microwave transparency.

The reaction vessel may be connected to a microwave generator so that microwaves may be irradiated to the reaction mixture therein. The microwave generator may be, for example, commercially available. The microwave generator may be, for example, a microwave reactor manufactured by CEM (model no. 908005). The reaction vessel may include a channel which is connected to the inlet and the outlet such that a fluid flows therethrough. The channel is connected to a pump to control fluid flow.

The reaction vessel may also be connected to a detector for detecting a substance. The detector may include an infrared (IR) sensor, high performance liquid chromatography (HPLC), a mass-spectrophotometer (MS), etc.

In the method, the *Cannabis* sp. plant may include *Cannabis* sp., such as *Cannabis* chemovars, *Cannabis sativa, Cannabis indica, Cannabis ruderalis*, etc., wild sp. thereof, variants thereof, mutants thereof, hybrids thereof, and plants including cannabinoid, etc. Further, the *Cannabis* sp. plant may be a living plant or a dried or non-dried plant. Further, the *Cannabis* sp. plant may be leaves, flower buds, seeds, nuts, trichomes, flower bracts, stems, roots, or any part including cannabinoids. Further, the *Cannabis* sp. plant may be a dioecious plant, and its cannabinoid content may vary depending on female and male plants. The *Cannabis* sp. plant may be a female plant, a male plant, or a mixture thereof. The *Cannabis* sp. plant may be any one as long as it includes one or more of CBD and THC.

In the method, the acid may be any acid effective in converting one or more of CBD and THC into CBN under conditions of continuously irradiating microwaves to the reaction mixture. The acid may be a Lewis acid. The acid may be, for example, an organic acid or an inorganic acid. The acid may be a sulfonic acid. The acid may be an acid having a structure of Formula I.

(Formula 1)

In Formula I, R1 is H, a C5-C12 aryl group, a C1-C12 alkyl group, a C3-C12 cycloalkyl group, a C3-C12 cycloketone group, or a C6-C12 arylalkyl group, and the aryl, alkyl, cycloalkyl, cycloketone, or arylalkyl group may have one or more substituents selected from the group consisting of halogen and a C1-C6 alkyl group. In a specific embodiment, R1 is a C6-C12 aryl group, a C1-C6 alkyl group, a C6-C12 cycloalkyl group, a C6-C12 cycloketone group, or a C6-C10 arylalkyl group, and the aryl, alkyl, cycloalkyl, cycloketone, or arylalkyl group may have one or more substituents selected from the group consisting of halogen and a C1-C6 alkyl group. In a specific embodiment, R1 may be a phenyl group, a benzyl group, a tolyl group, a biphenyl group, a naphthyl group, a C1-C8 alkyl group, a C6-C12 cycloalkyl group, or a C7-C12 arylalkyl group. The sulfonic acid is, for example, methanesulfonic acid (MSA), benzenesulfonic acid, naphthalenesulfonic acid, toluenesulfonic acid containing para-toluenesulfonic acid (p-toluensulfonic acid, PTSA), or camphor-10-sulfonic acid (CSA). The Lewis acid may also be formic acid, acetic acid, propionic acid, lactic acid, butyric acid, isobutyric acid, valeric acid, hexanoic acid, heptanoic acid, decanoic acid, lauric acid, myristic acid, C15-C18 fatty acid, fumaric acid, itaconic acid, malic acid, glutaric acid, glucaric acid, oxalic acid, adipic acid, pimelic acid, suberic acid, azelaic acid, sebacic acid, dodecanedioic acid, glutaconic acid, isocitric acid, citric acid, tartaric acid, succinic acid, fumaric acid, maleic acid, malonic acid, mandelic acid, malic acid, phthalic acid, hydrochloric acid, sulfuric acid, potassium hydrogensulfate, sodium hydrogensulfate, perchloric acid, or nitric acid.

The term "alkyl" refers to a straight or branched saturated hydrocarbon group. The alkyl may include, for example, methyl, ethyl, n-propyl, isopropyl, n-butyl, isobutyl, t-butyl, n-pentyl, isopentyl, neopentyl, n-hexyl, n-heptyl, n-octyl, n-nonyl or n-decyl.

The term "aryl" refers to an aromatic ring in which each atom forming a ring is a carbon atom. The ring may be a monocyclic or polycyclic ring. The polycyclic ring may include those having a fused ring (e.g., naphthalene) or a non-fused ring (e.g., biphenyl). The polycyclic ring may have, for example, 2 rings, 3 rings, or 4 rings. The aryl group has, for example, 5 or more, 6 or more, 7 or more, 8 or more, 9 or more, 10 or more, 5 to 12, 5 to 10, or 6 to 10 carbon ring atoms. The aryl group includes, for example, phenyl, naphthalenyl (e.g., naphthalen-1-yl and naphthalen-2-yl), and biphenyl.

The term "cycloalkyl" refers to a non-aromatic carbon ring in which each atom forming a ring is a carbon atom. The cycloalkyl may be monocyclic or polycyclic. The polycyclic may be, for example, those having 2, 3, or 4 fused rings. The cycloalkyl may include those fused to an aromatic ring. The cycloalkyl includes, for example, 3 or more, 4 or more, 5 or more, 6 or more, 7 or more, 3 to 10, 3 to 7, 5 to 7, or 5 to 6 ring carbon atoms. The cycloalkyl includes cyclopropyl, cyclobutyl, cyclopentyl, cyclohexyl, cycloheptyl, cyclohexadienyl, cycloheptatrienyl, norbornyl, norcanyl, and adamantyl.

The term "cycloketone" refers to "cycloalkyl" having a ketone group. In other words, the "cycloketone" indicates that each atom forming the ring includes a non-aromatic carbon ring which is a carbon atom, and one or more of carbon atoms forming the ring form a ketone group.

The term "arylalkyl" refers to alkyl substituted with aryl.

The term "halogen" refers to fluoro, chloro, bromo, or iodo.

In the method, the acid may be 1 time to 50 times with respect to CBD included in the reaction sample on a molar basis. The concentration of the acid may be, for example, 1 time to 40 times, 1 time to 30 times, 1 time to 20 times, 1 time to 10 times, 10 times to 50 times, 10 times to 40 times, 10 times to 30 times, 10 times to 20 times, 20 times to 50 times, 20 times to 40 times, 20 times to 30 times, 30 times to 50 times, 30 times to 40 times, or 40 times to 50 times with respect to CBD included in the reaction sample on a molar basis. The Lewis acid may have, for example, a concentration of 0.004 M to 2.0 M. The Lewis acid may have a concentration of, for example, 0.004 M to 2.0 M, 0.04 M to 1.5 M, 0.4 M to 1.0 M, 0.02 M to 0.12 M, 0.04 M to 0.12 M, 0.08 M to 0.12 M, 0.02 M to 0.08 M, or 0.04 M to 0.08 M.

In the method, the extract may be obtained by a method including contacting any solvent with the *Cannabis* sp. plant. The solvent may be a solvent capable of extracting or dissolving cannabinoid, for example, one or more of CBD and THC in the *Cannabis* sp. plant. The solvent may be water, a protonic solvent, an aprotonic solvent, or a mixture thereof. The protonic solvent may be C1-C6 alcohol or C1-C4 alcohol. The aprotonic solvent may be C3-C10 ester, C3-C10 ketone, or unsubstituted or halogenated C1-C6 hydrocarbon. The extract may have an increased total content of one or more of CBD and THC which are cannabinoids.

The total content of cannabinoids including one or more of CBD and THC in the extract may be 1% or more, or 5% or more, for example, 1% to 90%, 5% to 90%, 5% to 80%, 5% to 70%, 5% to 60%, 5% to 50%, 5% to 40%, 5% to 30%, 5% to 20%, 5% to 10%, 5% to 9%, 5% to 8%, 5% to 7%, or 5% to 6%, based on the weight. The extract has no phase separation when concentrated, and may have high solubility.

In the method, the extract may be obtained by a method including incubating a reaction mixture including cannabinoids and a solvent, for example, a protonic solvent. The incubating may be performed at 20° C., 25° C., 30° C., or 35° C. to a reflux temperature of a single solvent or a mixed solvent used.

In the method, the protonic solvent may be ethanol, n-propanol, isopropanol, n-butanol, a mixture thereof, or an aqueous solution thereof.

In the method, the extract may be obtained by a method including incubating a reaction mixture including cannabinoids and a solvent, for example, an aprotonic solvent. The incubating may be performed at 20° C., 25° C., 30° C., or 35° C. to a reflux temperature of a single solvent or a mixed solvent used.

In the method, the aprotonic solvent may be ethyl acetate, acetone, 2-butanone, chloroform, dichloromethane, hexane, or a mixture thereof.

In the method, the *Cannabis* sp. plant may be leaves, flower buds, seeds, nuts, trichomes, flower bracts, stems, roots, or any part including cannabinoids.

In the method, the content of cannabinoid including one or more CBD and THC in the extract may be 1% or more, or 5% or more, for example, 1% to 90%, 5% to 90%, 5% to 80%, 5% to 70%, 5% to 60%, 5% to 50%, 5% to 40%, 5% to 30%, 5% to 20%, 5% to 10%, 5% to 9%, 5 to 8%, 5% to 7%, or 5% to 6%, based on the total weight of the extract.

Conversion of CBD included in the cannabis plant or the extract thereof into $\Delta^9$-THC through cyclization and/or conversion of $\Delta^9$-THC into CBN through aromatization may be achieved by microwave irradiation.

In the method, an appropriate temperature of the microwave irradiation may be selected according to the solvent, the content of one or more of CBD and THC included in the reaction mixture, the content of $\Delta^9$-THC or CBN in a final product, or a ratio of $\Delta^9$-THC or CBN to CBD. The microwave irradiation may be carried out at 60° C. to 150° C., for example, 60° C. to 140° C., 60° C. to 130° C., 60° C. to 120° C., 60° C. to 110° C., 60° C. to 100° C., 60° C. to 90° C., 60° C. to 80° C., 60° C. to 70° C., 70° C. to 140° C., 70° C. to 130° C., 70° C. to 120° C., 70° C. to 110° C., 70° C. to 100° C., 70° C. to 90° C., 70° C. to 80° C., 80° C. to 140° C., 80° C. to 130° C., 80° C. to 120° C., 80° C. to 110° C., 80° C. to 100° C., 80° C. to 90° C., 90° C. to 140° C., 90° C. to 130° C., 90° C. to 120° C., 90° C. to 110° C., 90° C. to 100° C., 100° C. to 140° C., 100° C. to 130° C., 100° C. to 120° C., 100° C. to 110° C., or 110° C. to 120° C.

In the method, the microwave irradiation may be carried out for a time sufficient to convert CBD into $\Delta^9$-THC or CBN, or to convert THC into CBN. The microwave irradiation may be carried out for a time sufficient to convert CBD into $\Delta^9$-THC or CBN, or to convert THC into CBN while retaining the reaction mixture in the vessel. The retention time may be controlled by the pump. Further, the retention time may be controlled by controlling the flow rate according to a ratio between the length in the flow direction and the height of the vessel.

The microwave irradiation time may vary depending on the thickness and length of the tube, the reaction temperature, a microwave output power, the solvent used, and use of the final product. As used herein, the "microwave irradiation time" refers to the time for which microwaves are irradiated to the reaction mixture, independent of an operating time of the microwave generator. The microwave irradiation time represents the time for which the reactants are exposed to microwaves while flowing through the tube in the reactor. Therefore, even though the microwave generator is turned on, if the reactants are not exposed to microwaves, it is not included in the microwave irradiation time. The microwave irradiation time becomes longer as the flow rate is slower. The microwave irradiation time may be 5 minutes to 180 minutes, for example, 10 minutes to 180 minutes, 10 minutes to 150 minutes, 10 minutes to 100 minutes, 10 minutes to 90 minutes, 20 minutes to 180 minutes, 20 minutes to 150 minutes, 20 minutes to 100 minutes, 20 minutes to 90 minutes, 30 minutes to 180 minutes, 30 minutes to 150 minutes, 30 minutes to 100 minutes, 30 minutes to 90 minutes, 5 minutes to 30 minutes, 5 minutes to 20 minutes, 5 minutes to 10 minutes, 10 minutes to 30 minutes, 10 minutes to 20 minutes, or 20 minutes to 30 minutes.

In the method, the microwave irradiation may be carried out while flowing the reaction mixture via the pump at a flow rate of 0.010 mL to 10 mL per min. The flow rate may be, for example, 0.010 mL to 5.0 mL, 0.010 mL to 2.0 mL, 0.010 mL to 1.0 mL, 0.010 mL to 0.50 mL, 0.010 mL to 0.10 mL, 0.10 mL to 10 mL, 0.10 mL to 5.0 mL, 0.10 mL to 2.0 mL, 0.10 mL to 1.0 mL, 0.10 mL to 0.50 mL, 0.50 mL to 10 mL, 0.50 mL to 5.0 mL, 0.50 mL to 2.0 mL, 0.50 mL to 1.0 mL, 1.0 mL to 10 mL, 1.0 mL to 5.0 mL, 1.0 mL to 2.0 mL, 2.0 mL to 10 mL, 2.0 mL to 5.0 mL, or 5.0 mL to 10 mL per min.

In the method, the microwave irradiation may be carried out under pressure. The microwave irradiation may be carried out under a pressure of more than 1 atm to 100 atm, for example, 2 atm to 100 atm, 2 atm to 50 atm, 2 atm to 30 atm, 2 atm to 20 atm, or 2 atm to 15 atm.

In the microwave irradiation of the method, the microwave output power may be 3 W to 6 kW, for example, 10 W to 6 kW, 10 W to 3 kW, 10 W to 1 kW, 10 W to 500 W, 10 W to 100 W, 10 W to 70 W, 10 W to 50 W, or 3 W to 50 W.

In the method, the microwave irradiation indicates a thermal reaction of heating the cannabis plant or the extract thereof, or the sample including one or more of CBD and THC by irradiating microwaves thereto. The microwave may be microwave having a frequency of 300 MHz to 300 GHz, for example, 1000 MHz to 100 GHz, 1000 MHz to 50 GHz, 1000 MHz to 10 GHz, or 1000 MHz to 5 GHz. In a specific embodiment, the microwave irradiation may be carried at 500 MHz to 5000 MHz, 500 MHz to 4000 MHz, 1000 MHz to 5000 MHz, 1000 MHz to 3000 MHz, 2000 MHz to 4000 MHz, or 2000 MHz to 3000 MHz.

In the method, the produced or isolated cannabinoids may be THC and/or CBN.

In the microwave irradiation of the method, the solvent is not particularly limited. The solvent may be, for example, a protonic polar solvent, or an aprotonic polar or non-polar solvent. The protonic polar solvent may be water, methanol, ethanol, propanol, isopropanol, or butanol. The aprotonic polar solvent may be dichloromethane, tetrahydrofuran, ethyl acetate, dimethylformamide, dimethyl sulfoxide, acetone, 2-butanone, or hexamethylphosphoramide. The non-polar solvent may be pentane, hexane, chloroform, or diethyl ether. The solvent may be C1-C12 alcohol, C3-C10 ester, C3-C10 ketone, C1-C6 unsubstituted or halogenated hydrocarbon, C2-C10 cyclic ether, a mixture thereof, or a mixture of one or more of the solvents and water. The solvent may be ethanol, propanol, butanol, ethyl acetate, acetone, 2-butanone, chloroform, dichloromethane, hexane, a mixture thereof, or an aqueous solution thereof. The hydrocarbon may be alkane, alkene, or alkyne. The aqueous solution may be a 50% to 99% ethanol aqueous solution. The C1-C12 alcohol may be C1-06 alcohol, C1-C4 alcohol, or C2-C5 alcohol.

The microwave irradiation may be carried out to convert 10% to 100%, for example, 20% to 100%, 25% to 100%, 30% to 100%, 50% to 100%, 80% to 100%, 90% to 100%, 95% to 100%, 97% to 100%, or 100% of one or more ingredients of CBD and THC included in the *Cannabis* sp. plant or the extract thereof into the CBN ingredient.

The reaction mixture may include one or more of CBD and THC dissolved in the solvent. One or more of CBD and THC may be included at a concentration of 1 ppm to a saturation concentration of one or more of CBD and THC for the corresponding solvent, 10 ppm to a saturation concentration of one or more of CBD and THC for the corresponding solvent, 50 ppm to a saturation concentration of one or more of CBD and THC for the corresponding solvent, 100 ppm to a saturation concentration of one or more of CBD and THC for the corresponding solvent, 200 ppm to a saturation concentration of one or more of CBD and THC for the corresponding solvent, 200 ppm to 10,000 ppm, 200 ppm to 5,000 ppm, 500 ppm to 10,000 ppm, 500 ppm to 5,000 ppm, or 500 ppm to 1,000 ppm.

The reaction mixture may include a cannabis extract including one or more of CBD and THC dissolved in the solvent. The extract may be included at a concentration of 1 ppm to a saturation concentration of one or more of CBD and THC for the corresponding solvent, 10 ppm to a saturation concentration of one or more of CBD and THC for the corresponding solvent, 50 ppm to a saturation concentration of one or more of CBD and THC for the corresponding solvent, 100 ppm to a saturation concentration of one or more of CBD and THC for the corresponding solvent, 200 ppm to a saturation concentration of one or more of CBD and THC for the corresponding solvent, 200 ppm to 10,000 ppm, 200 ppm to 5,000 ppm, 500 ppm to 10,000 ppm, 500 ppm to 5,000 ppm, or 500 ppm to 1,000 ppm.

In the method, the isolated cannabinoids may include 10% by weight to 100% by weight, for example, 10% by weight to 99% by weight, 10% by weight to 95% by weight, 10% by weight to 90% by weight, 20% by weight to 100% by weight, 20% by weight to 99% by weight, 20% by weight to 95% by weight, or 20% by weight to 90% by weight of $\Delta^9$-THC or CBN, based on the total weight of the isolate.

The method may include isolating cannabinoids from the microwave-irradiated reaction mixture. The isolating may be isolating $\Delta^9$-THC or CBN.

The isolating may include performing chromatography of the microwave-irradiated reaction mixture. The chromatography may be, for example, reverse-phase C18 column chromatography or reverse-phase semi-preparative high performance liquid chromatography. As a result, a single ingredient of $\Delta^9$-THC or CBN may be obtained by isolation through preparative liquid chromatography of the reaction mixture.

The isolation method by reverse-phase C18 column chromatography is an isolation method commonly used in a laboratory. Depending on the amount of a sample to be separated, a diameter of a glass column to be used and the amount of reverse-phase C18 to be used may vary. Generally, in the case of the glass column, a column having an internal diameter of 1 cm to 10 cm and a length of 10 cm to 100 cm, in which 50% to 70% of the height of the column is packed with reversed phase C18, may be used. A composition of an eluent to be used slightly varies depending on the amount of the sample and the silica gel column. For example, a mixed solvent having a volume ratio of methanol:water:ethyl acetate=1:1:0 to 1:0:0 to 0:0:1 may be sequentially used according to the mixing ratio.

The isolation conditions by reverse-phase semi-preparative HPLC may vary depending on the amount of the sample and the size of a column to be used. Generally, reverse-phase preparative HPLC (stationary phase: Luna C18(2) column, Phenomenex, particle size of 10 μm, length of 250 mm×10 mm) is prepared in a liquid chromatography (Shimadzu) instrument, and the sample dissolved in an initial eluent is injected, and then isolation may be performed while developing the eluent from acetonitrile:water=50:50 (v/v) to acetonitrile:water=100:0 (v/v) for 60 min to 90 min.

Still another aspect provides a composition including cannabinoid produced by the above method. The composition may include CBN alone or a combination of THC and CBN. The composition may be in the form of a mixture of substances, i.e., in a state in which THC or CBN is not purified into a single compound from the microwave-irradiated reaction mixture. The composition may be, for example, a processed extract.

Still another aspect provides a pharmaceutical composition including, as an active ingredient, the cannabinoids produced by the above method. The composition may be for antibacterial, analgesic, antidepressant, or insomnia treatment. The cannabinoids may be $\Delta^9$-THC or CBN. The cannabinoids may be a fraction, a single compound, or a mixture thereof. The pharmaceutical composition may further include a pharmaceutically acceptable carrier or diluent.

The cannabinoids has improved $\Delta^9$-THC or CBN efficacy due to a significantly high content of $\Delta^9$-THC or CBN, as compared with a processed product resulting from simple heat-treatment. $\Delta^9$-THC or CBN is known to have antibacterial, analgesic, antidepressant, or insomnia treatment effects. Therefore, these effects may be significantly increased by the microwave irradiation, as compared with a processed product resulting from simple heat-treatment.

Still another aspect provides a health functional food composition including, as an active ingredient, the cannabinoids isolated by the above method. The cannabinoids may be CBN. The cannabinoids may be a fraction, a single compound, or a mixture thereof. The food may be a functional food or a health functional food. The functional ingredient of the food is a safe food composition partially including the pharmaceutical ingredient, and may further include a carrier or diluent acceptable for use in foods.

Still another aspect provides a cosmetic composition including, as an active ingredient, the cannabinoids isolated by the above method. The cosmetics may be a general cosmetics or a functional cosmetics. $\Delta^9$-THC or CBN, known as a functional ingredient of cosmetics, may be a composition having an antioxidant or anti-inflammatory effect. The cosmetic composition may further include a carrier or diluent acceptable for use in cosmetics.

Still another aspect provides a method of treating a disease of an individual, the method including administering, to the individual, a composition including, as an active ingredient, the cannabinoids isolated by the above method. The disease may be cancer, epilepsy, diabetes, bacterial infection, osteoporosis, skin inflammation, pain, depression, or insomnia. The individual may be a mammal.

Still another aspect provides a cosmetic method, the method including applying, to an individual, a composition including, as an active ingredient, the cannabinoids isolated by the above method. The applying may be applying to the skin.

BRIEF DESCRIPTION OF THE DRAWINGS

The above and other aspects, features, and advantages of certain embodiments of the disclosure will be more apparent from the following description taken in conjunction with the accompanying drawings, in which.

Figure 25:
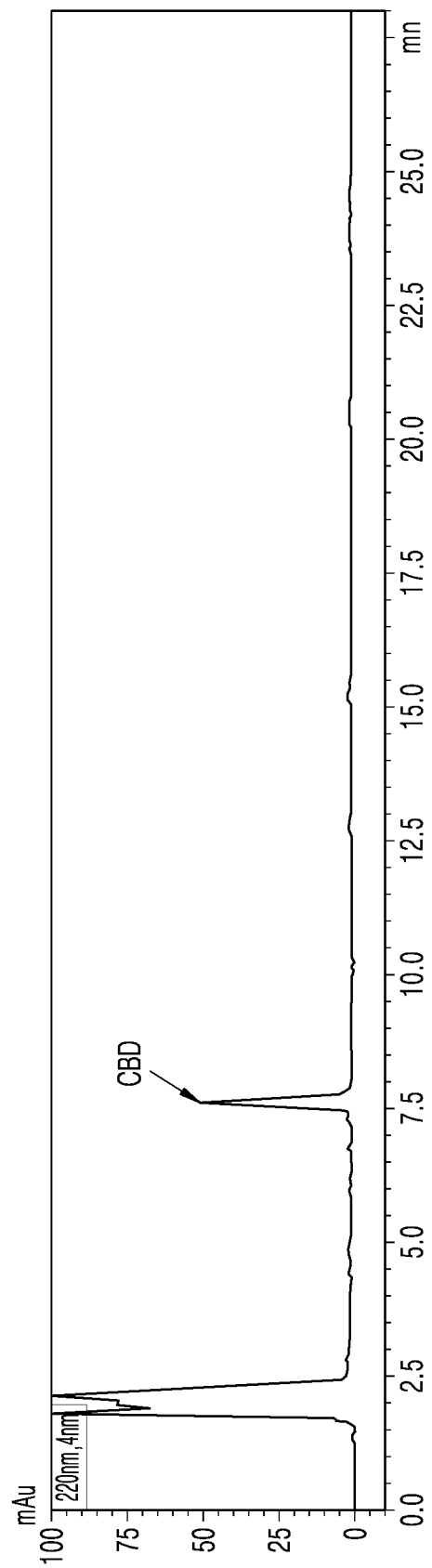
Figure 26:
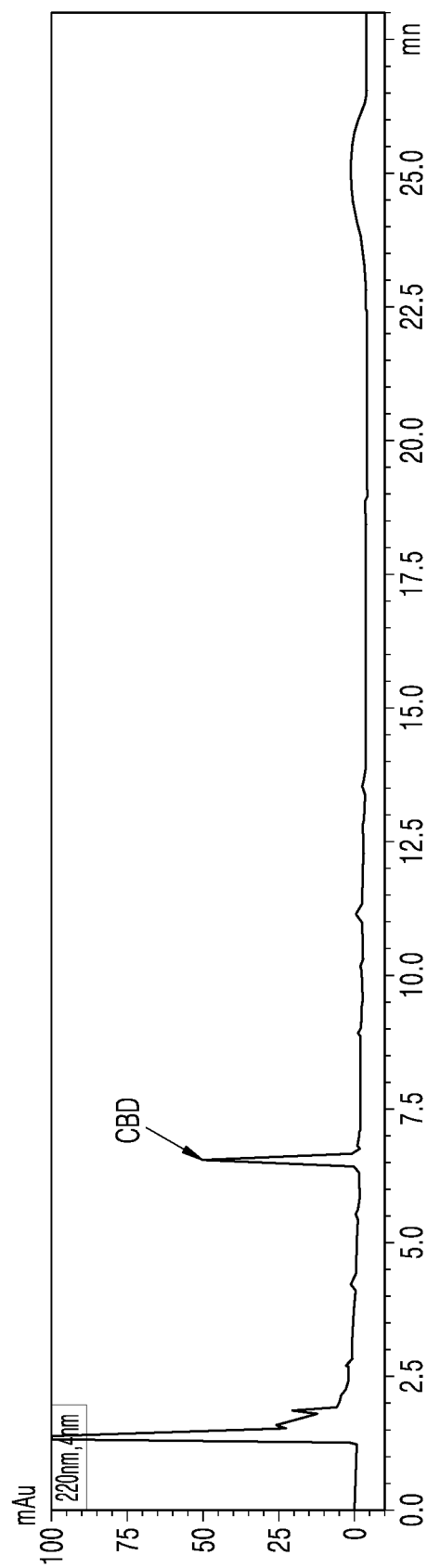
Figure 27:
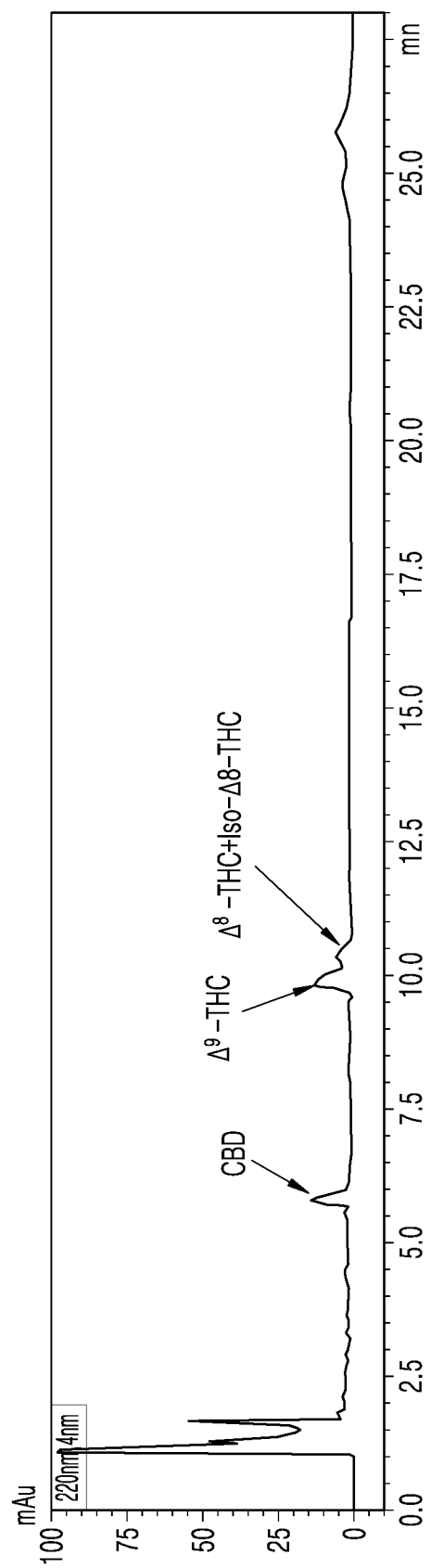
Figure 28:
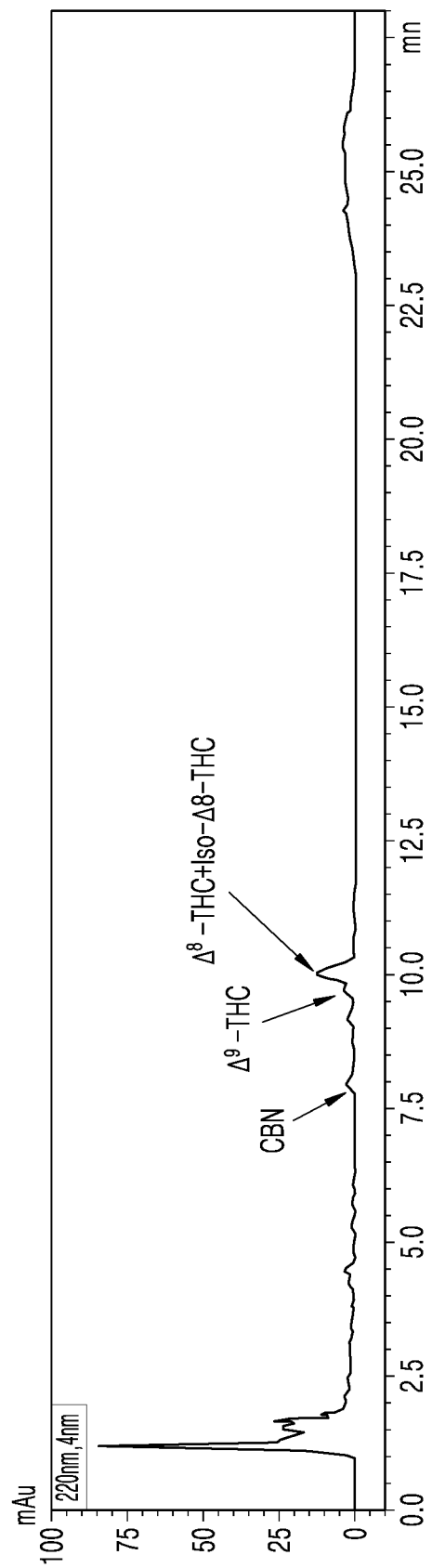
Figure 29:
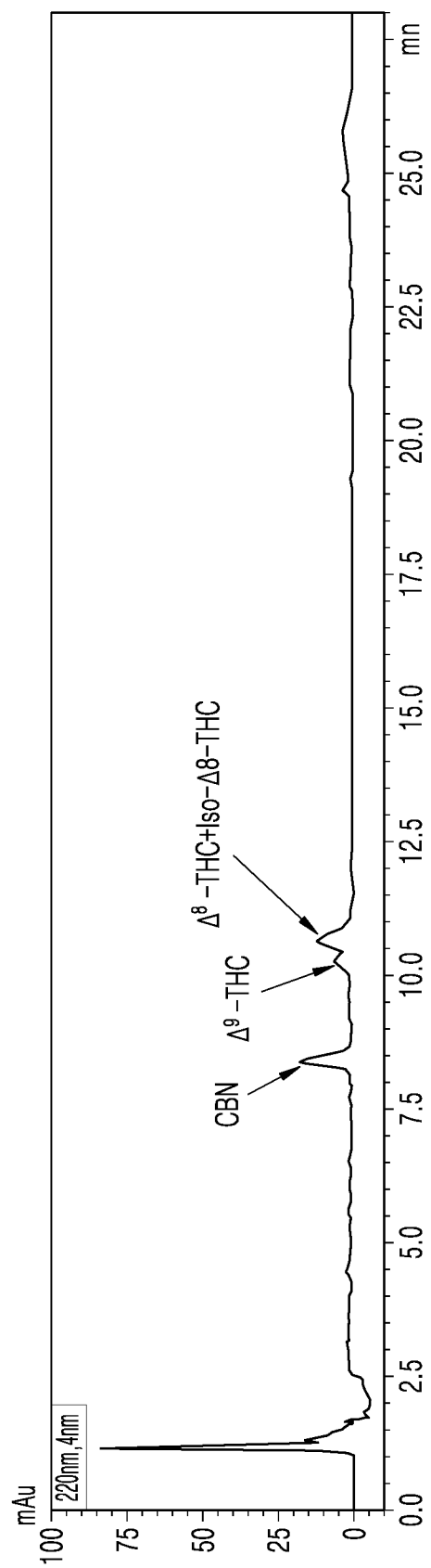
Figure 30:
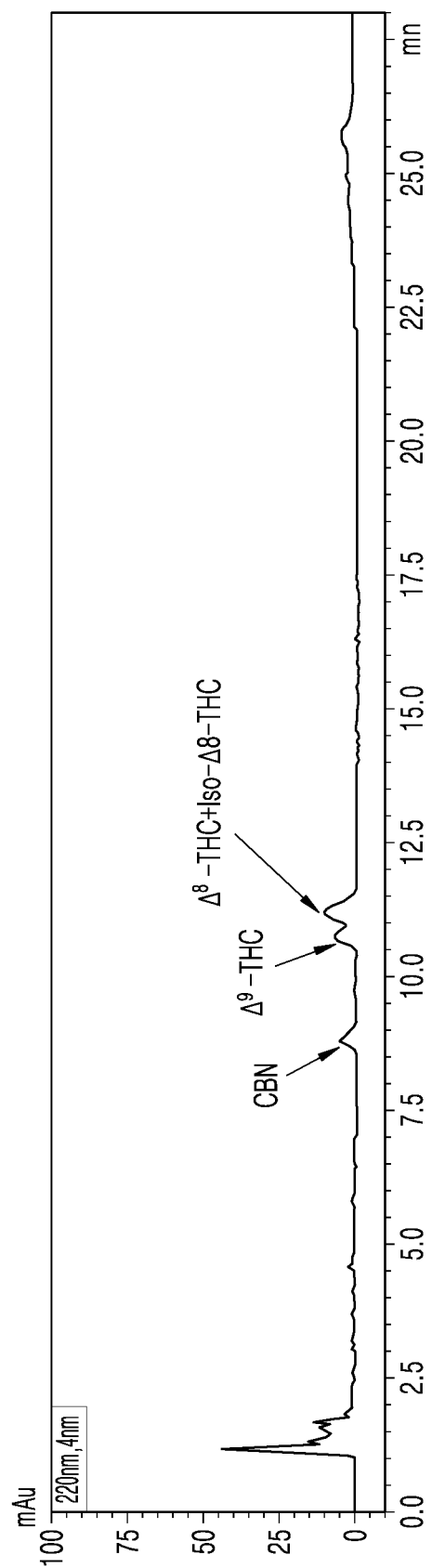
Figure 31:
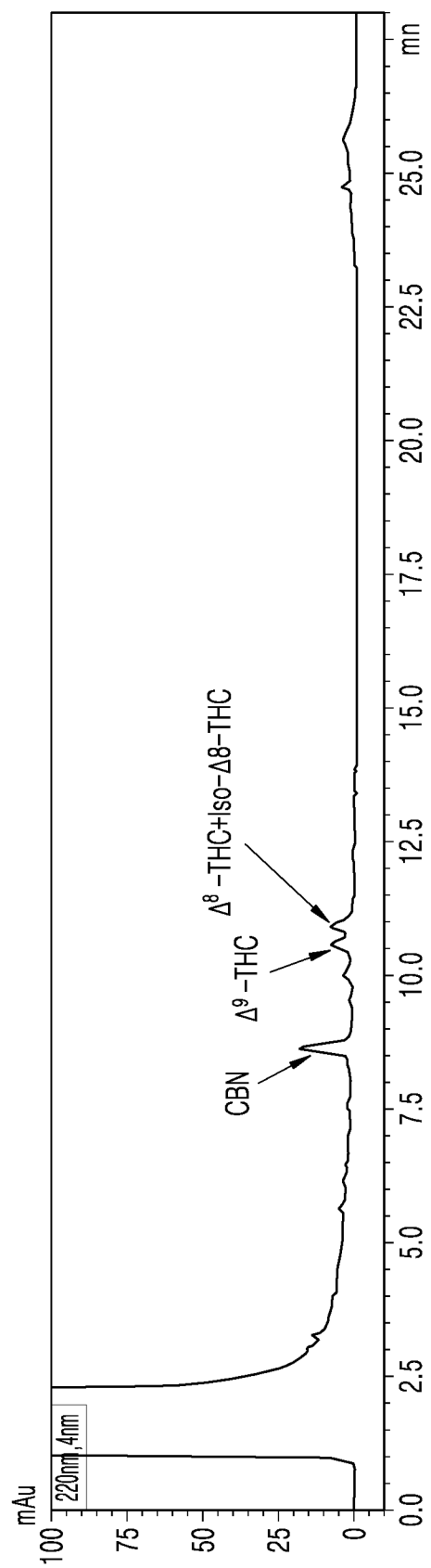
Figure 32:
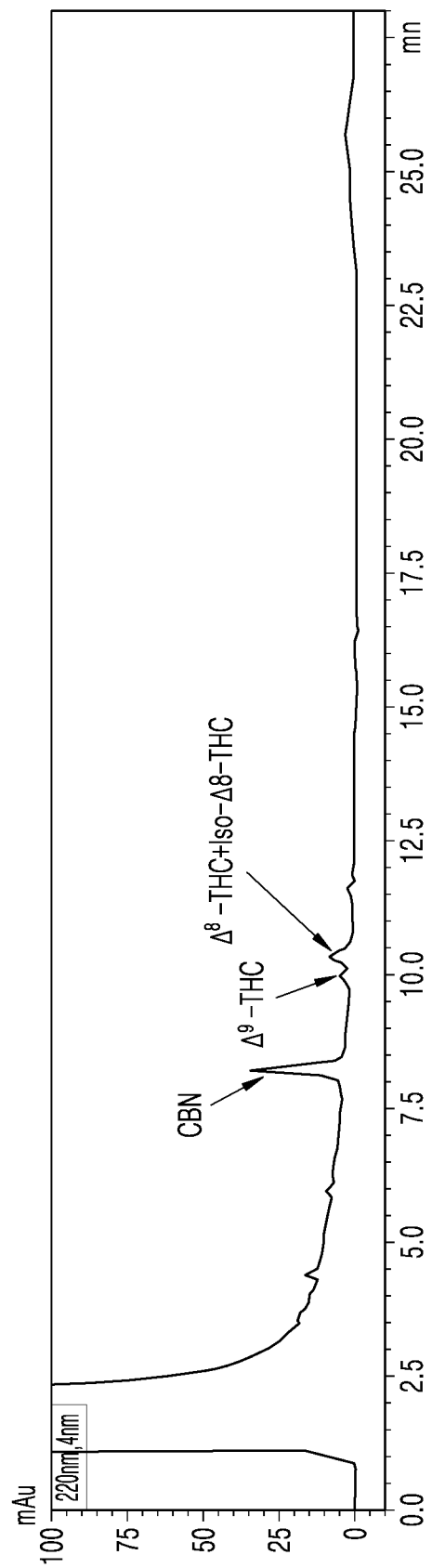
Figure 33:
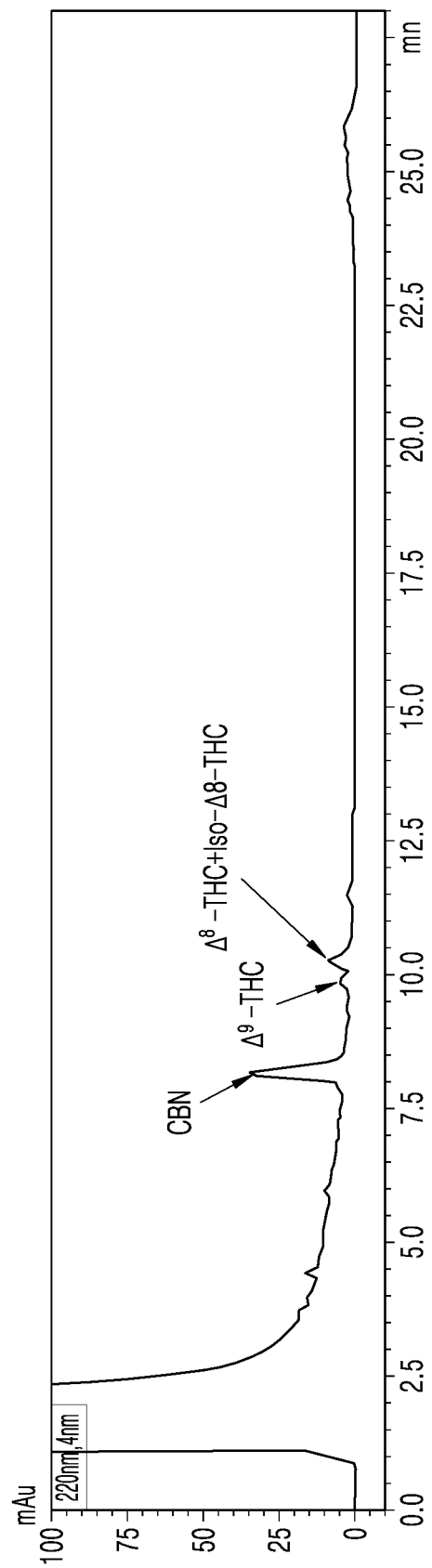
Figure 34:
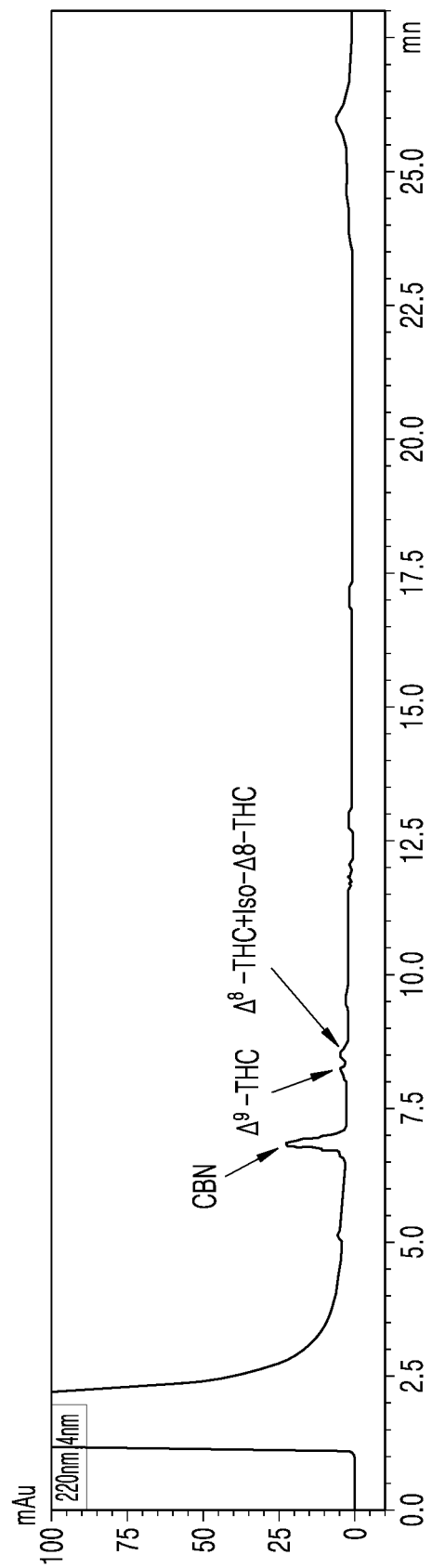
Figure 35:
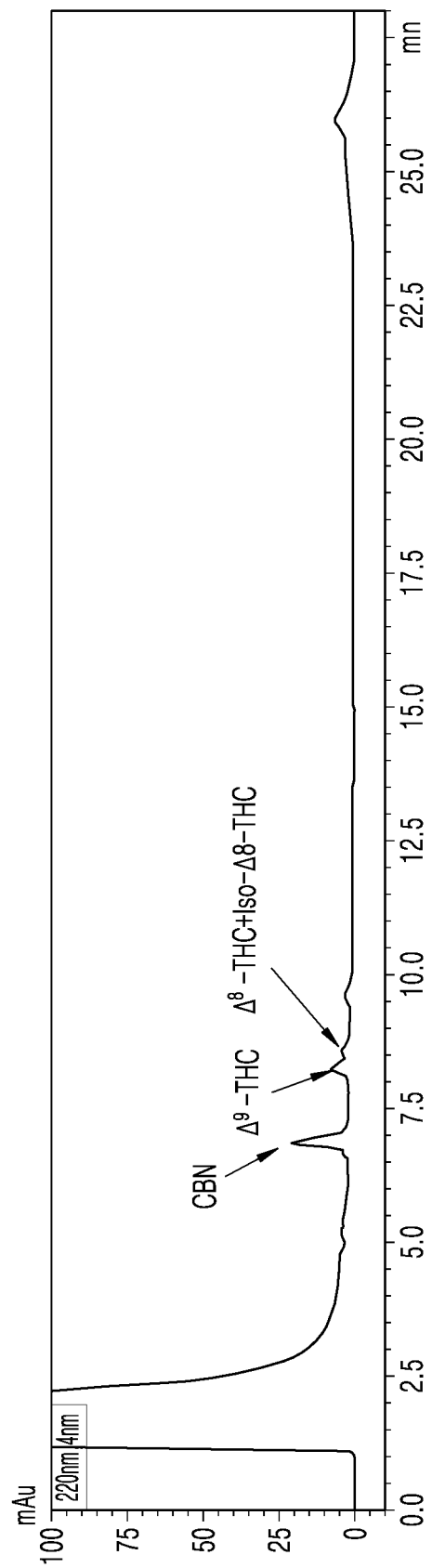
Figure 36:
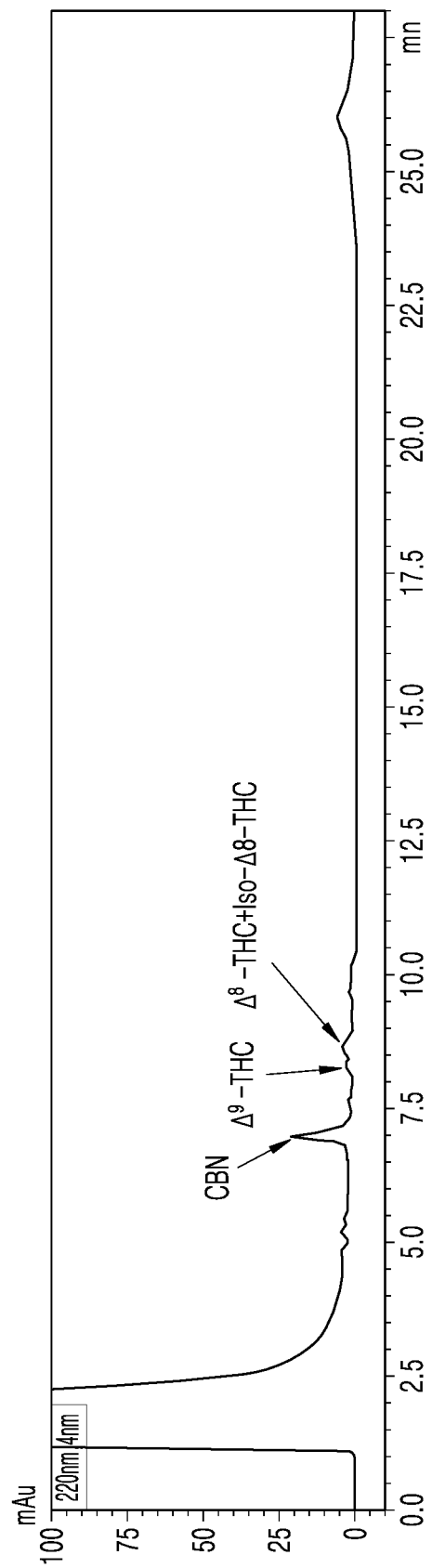

FIG. 25 shows a UPLC chromatogram for analyzing cannabinoid ingredients in a processed product obtained by microwave-irradiation for 30 minutes while adding 20 equivalent weights of sulfuric acid, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min;

FIG. 26 shows a UPLC chromatogram for analyzing cannabinoid ingredients in a processed product obtained by microwave-irradiation for 30 minutes while adding 20 equivalent weights of camphorsulfonic acid (CSA), relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min;

FIG. 27 shows a UPLC chromatogram for analyzing cannabinoid ingredients in a processed product obtained by microwave-irradiation for 30 minutes while adding 20 equivalent weights of methanesulfonic acid (MSA), relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min;

FIG. 28 shows a UPLC chromatogram for analyzing cannabinoid ingredients in a processed product obtained by microwave-irradiation for 30 minutes while adding 10 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min;

FIG. 29 shows a UPLC chromatogram for analyzing cannabinoid ingredients in a processed product obtained by microwave-irradiation for 30 minutes while adding 30 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min;

FIG. 30 shows a UPLC chromatogram for analyzing cannabinoid ingredients in a processed product obtained by microwave-irradiation for 30 minutes while adding 40 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min;

FIG. 31 shows a UPLC chromatogram for analyzing cannabinoid ingredients in a processed product obtained by microwave-irradiation for 10 minutes while adding 20 equivalent weights of PTSA, relative to the total weight of CBD and $\Delta^9$-THC, to a 200 ppm solution of the extract B of cannabis leaves in ethanol and applying the solution to a tube with a volume of 1.0 mL through a liquid-feeding pump at 80° C. at a flow rate of 0.10 mL/min;

FIG. 32 shows a UPLC chromatogram for analyzing cannabinoid ingredients in a processed product obtained by microwave-irradiation for 10 minutes while adding 20 equivalent weights of PTSA, relative to the total weight of CBD and $\Delta^9$-THC, to a 200 ppm solution of the extract B of cannabis leaves in ethanol and applying the solution to a tube with a volume of 1.0 mL through a liquid-feeding pump at 80° C. at a flow rate of 0.050 mL/min;

FIG. 33 shows a UPLC chromatogram for analyzing cannabinoid ingredients in a processed product obtained by microwave-irradiation for 30 minutes while adding 20 equivalent weights of PTSA, relative to the total weight of CBD and $\Delta^9$-THC, to a 200 ppm solution of the extract B of cannabis leaves in ethanol and applying the solution to a tube with a volume of 1.0 mL through a liquid-feeding pump at 80° C. at a flow rate of 0.033 mL/min;

FIG. 34 shows a UPLC chromatogram for analyzing cannabinoid ingredients in a processed product obtained by microwave-irradiation for 10 minutes while adding 20 equivalent weights of PTSA, relative to the total weight of $\Delta^9$-THC, to a 200 ppm solution of the extract C of cannabis leaves in ethanol and applying the solution to a tube with a volume of 1.0 mL through a liquid-feeding pump at 80° C. at a flow rate of 0.100 mL/min;

FIG. 35 shows a UPLC chromatogram for analyzing cannabinoid ingredients in a processed product obtained by microwave-irradiation for 20 minutes while adding 20 equivalent weights of PTSA, relative to the total weight of $\Delta^9$-THC, to a 200 ppm solution of the extract C of cannabis leaves in ethanol and applying the solution to a tube with a volume of 1.0 mL through a liquid-feeding pump at 80° C. at a flow rate of 0.050 mL/min; and FIG. 36 shows a UPLC chromatogram for analyzing cannabinoid ingredients in a processed product obtained by microwave-irradiation for 30 minutes while adding 20 equivalent weights of PTSA, relative to the total weight of $\Delta^9$-THC, to a 200 ppm solution of the extract C of cannabis leaves in ethanol and applying the solution to a tube with a volume of 1.0 mL through a liquid-feeding pump at 80° C. at a flow rate of 0.033 mL/min.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in more detail with reference to exemplary embodiments. However, these exemplary embodiments are only for illustrating the present disclosure, and the scope of the present disclosure is not limited to these exemplary embodiments.

Example 1: Preparation of CBN by Continuous Microwave Irradiation to Cannabis Extract In the following exemplary embodiments, cannabis was incubated in a solvent to obtain a cannabis extract, which was then continuously irradiated with microwaves to efficiently synthesize CBN.

1. Preparation of Cannabis Extract
(1) Preparation of Cannabis Ethyl Acetate Extract from Korean Hemp (Including Only CBD)

The Korean Hemp was provided by JayHempKorea Ltd., located in Sangju city, Gyeongsangbuk-do, South Korea, through assignment/transfer approval processes under drug (cannabis) research permission (No. 1564) obtained from the Ministry of Food and Drug Safety and Seoul Regional Food and Drug Administration. Cannabis seed shells, cannabis leaves, cannabis stems, and cannabis roots were harvested in October, 2018, and used. Cannabis leaves having a relatively high content of cannabinoids among the parts of cannabis were dried using a drying oven (Hanbaek Science Co. Ltd., HB-502L) at 80° C. for 48 hours, and then finely cut. 5 g of the dried cannabis leaves and 50 mL of ethyl acetate were added in a 250 mL Erlenmeyer flask, and microwave-irradiated using an ultrasonic processor (Sonics, VC505) at 40% power of the instrument for 1 hour, i.e., 200 W, and then incubated at room temperature for 24 hours. This procedure was repeated twice.

The liquid extract, which was obtained by filtering the microwave-irradiated mixture of the dried cannabis leaves and ethyl acetate through a filter, was concentrated by evaporation under reduced pressure to obtain 0.44 g of a dry cannabis leave extract including CBD. Components of this extract were analyzed using UPLC-MS instruments (SHIMADZU), and as a result, $\Delta^9$-THC was not detected. Hereinafter, this extract was referred to as extract A.

(2) Preparation of Cannabis Ethyl Acetate Extract from Cannabis (Including CBD and $\Delta^9$-THC)

The Cannabis was provided by Andongpo Association, Inc., located in Andong city, Gyeongsangbuk-do, South Korea, through assignment/transfer approval processes under drug (cannabis) research permission (No. 1564) obtained from the Ministry of Food and Drug Safety and Seoul Regional Food and Drug Administration. Cannabis leaves were harvested in July, 2019, and dried using a drying oven (Hanbaek Science Co. Ltd., HB-502L) at 80° C. for 48 hours, and then finely cut and used. 5 g of the dried cannabis leaves and 50 mL of ethyl acetate were added in a 250 mL Erlenmeyer flask, and microwave-irradiated using an ultrasonic processor (Sonics, VC505) at 40% power of the instrument for 1 hour, i.e., 200 W, and then incubated at room temperature for 24 hours. This procedure was repeated twice.

The liquid extract, which was obtained by filtering the microwave-irradiated mixture of the dried cannabis leaves and ethyl acetate through a filter, was concentrated by evaporation under reduced pressure to obtain 0.41 g of a dry cannabis leave extract including CBD and $\Delta^9$-THC. Components of this extract were analyzed using UPLC-MS instruments (SHIMADZU), and as a result, CBD and $\Delta^9$-THC were detected. Hereinafter, this extract was referred to as extract B.

(3) Preparation of Cannabis Ethyl Acetate Extract from Indigenous Species of Cannabis (Including Only $\Delta^9$-THC)

An indigenous species of cannabis was provided by Andongpo Association, Inc., located in Andong city, Gyeongsangbuk-do, South Korea, through assignment/transfer approval processes under drug (cannabis) research permission (No. 1564) obtained from the Ministry of Food and Drug Safety and Seoul Regional Food and Drug Administration. Cannabis leaves were harvested in July, 2019, and dried using a drying oven (Hanbaek Science Co. Ltd., HB-502L) at 80° C. for 48 hours, and then finely cut and used. 5 g of the dried cannabis leaves and 50 mL of ethyl acetate were added in a 250 mL Erlenmeyer flask, and microwave-irradiated using an ultrasonic processor (Sonics, VC505) at 40% power of the instrument for 1 hour, i.e., 200 W, and then incubated at room temperature for 24 hours. This procedure was repeated twice.

The liquid extract, which was obtained by filtering the microwave-irradiated mixture of the dried cannabis leaves and ethyl acetate through a filter, was concentrated by evaporation under reduced pressure to obtain 0.25 g of a dry cannabis leave extract including $\Delta^9$-THC. Components of this extract were analyzed using UPLC-MS instruments (SHIMADZU), and as a result, only $\Delta^9$-THC was detected. Hereinafter, this extract was referred to as extract C.

2. Manufacture of Continuous Microwave Processing Equipment

As a continuous microwave processing equipment, a microwave irradiator (model no. 908005) manufactured by CEM Company (USA) was used, and a tube made of PTFE and PFA was inserted into a reaction chamber of a 10-mL flow cell accessory (model no. 908910) to manufacture a continuous reactor. Thereafter, the chamber of the continuous reactor was filled with water, and a liquid-feeding pump (YMC-KP series) was connected to one end of the inserted tube, i.e., to a tube at an inlet through which the reaction mixture is applied, and a back pressure regulator of 75 psi (UPCHURCH, P-786) was connected to the other end, i.e., to a tube at an outlet through which the reaction mixture is discharged. The tube had an outer diameter (O.D.) of 1/16 inch, an inner diameter (I.D.) of 1.0 mm, a length of 127.4 cm, and an inner tube volume of 1.0 mL.

Figure 1:
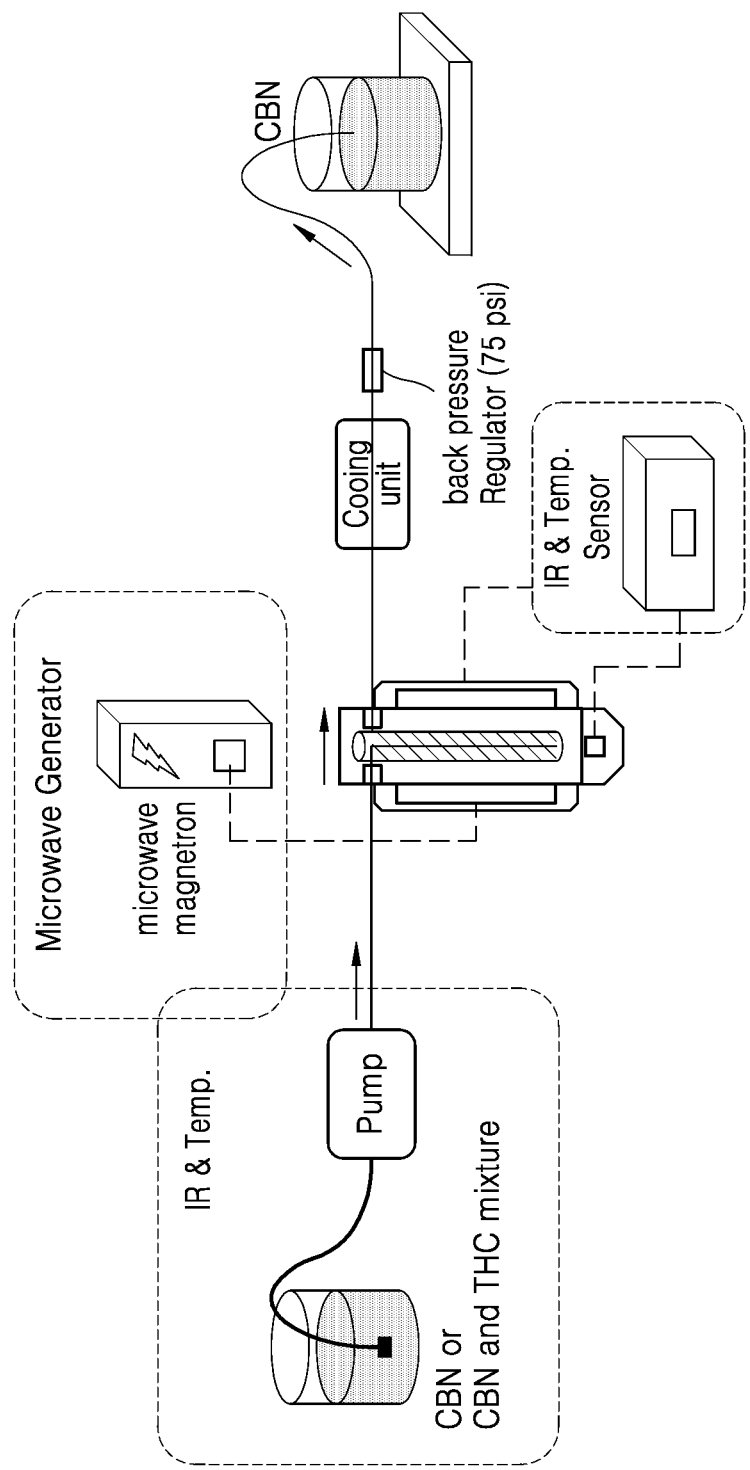
FIG. 1 shows an illustration of continuous microwave processing equipment.

FIG. 1 shows an illustration of continuous microwave processing equipment.

3. Continuous Microwave Processing of Cannabis Leaf Extracts A and B (1) Experimental Group The cannabis leaf extracts A and B were subjected to continuous microwave processing. In detail, the cannabis leaf extract A was dissolved at a concentration of 200 ppm in ethanol, and then 20 equivalent weights of p-toluenesulfonic acid (PTSA), relative to CBD, was added thereto. A reaction temperature of the continuous reactor was set at 60° C., and continuous microwave processing was carried out at a microwave maximum power of 50 W and a frequency of 2450 MHz for 40 minutes (experimental group 1) and 60 minutes (experimental group 2). In such a manner, experiments were performed at 70° C. for 40 min (experimental group 3) and at 70° C. 60 min (experimental group 4), at 80° C. for 20 min (experimental group 5), at 90° C. for 20 min (experimental group 6), at 100° C. for 20 min (experimental group 7), at 110° C. for 20 min (experimental group 8), and at 120° C. for 20 min (experimental group 9). Thereafter, a reaction temperature of the continuous reactor was set at 100° C., and microwave irradiation was performed for 30 min (experimental group 10) and 40 minutes (experimental group 11) to obtain microwave-irradiated processed products, respectively.

Next, the solvent was replaced by isopropanol (experimental group 12), ethyl acetate (experimental group 13), butanol (experimental group 14), and 70% ethanol aqueous solution (experimental group 15), and microwave irradiation was performed to obtain processed products, respectively.

Next, the reaction temperature of the continuous reactor was set at 100° C., and 20 equivalent weights of sulfuric acid (experimental group 16), camphorsulfonic acid (CSA) (experimental group 17), or methanesulfonic acid (MSA) (experimental group 18), relative to CBD, was added for 30 minutes to perform experiments, and 10 equivalent weights (experimental group 19), 30 equivalent weights (experimental group 20), or 40 equivalent weights (experimental group 21) of PTSA was added, and each was irradiated with microwaves to obtain processed products, respectively.

Next, the cannabis leaf extract B was dissolved at a concentration of 200 ppm in ethanol, and then 20 equivalent weights of PTSA, relative to the total weight of CBD and $\Delta^9$-THC, was added thereto. A reaction temperature of the continuous reactor was set at 80° C., and continuous microwave processing was carried out at a microwave maximum power of 50 W and a frequency of 2450 MHz for 10 minutes (experimental group 22), 20 minutes (experimental group 23) and 30 minutes (experimental group 24) to obtain processed products, respectively.

Next, the cannabis leaf extract C was dissolved at a concentration of 200 ppm in ethanol, and then 20 equivalent weights of PTSA, relative to the total weight of $\Delta^9$-THC, was added thereto. A reaction temperature of the continuous reactor was set at 80° C., and continuous microwave processing was carried out at a microwave maximum power of 50 W and a frequency of 2450 MHz for 10 minutes (experimental group 25), 20 minutes (experimental group 26) and 30 minutes (experimental group 27) to obtain processed products, respectively.

Each reaction time was controlled by controlling the flow rate of the liquid-feeding pump, and the power was 3 W to 50 W during microwave irradiation, and the content analysis was performed according to an analysis method of the following section 4. The reaction time according to the flow rate was as follows: 5 min at 0.2 mL/min, 10 min at 0.1 mL/min, 20 min at 0.05 mL/min and 30 min at 0.033 mL/min, 40 min at 0.025 mL/min, and 60 min at 0.017 mL/min. Here, the reaction time represents the time for which the reactants remain in the tube in the continuous reactor. During the microwave irradiation, the power may vary depending on the size of the inner diameter of the tube.

(2) Control Group

For experiments of control groups, the cannabis leaf extract A was irradiated with microwaves in a batch manner, instead of the continuous manner. In detail, the extract A of dry cannabis leaves was dissolved at a concentration of 200 ppm in ethanol, and then 20 equivalent weights of PTSA, relative to CBD, was added thereto. A reaction temperature of a batch-type reactor was set at 80° C., and heat treatment was carried out for 30 minutes (control group 1) and 60 minutes (control group 2) to obtain processed products, respectively.

4. Analysis of Cannabinoids in Extracts and Continuous or Batch-Type Microwave-Processed Products (1) Experimental Method Based on values of CBD, $\Delta^9$-THC, and CBN calibration curves, cannabinoids in the cannabis extracts A, B, and C, and the processed extracts obtained by batch-type or continuous microwave irradiation thereof were analyzed, and repeated in triplicate to confirm reproducibility. As for CBD, $\Delta^9$-THC, and CBN single ingredients used in the experiments, CBD with purity of 96.3%, $\Delta^9$-THC with purity of 96.8%, and CBN with purity of 96.7% directly isolated from the cannabis leaf raw material were used. According to the general calibration curve analysis method, CBD, $\Delta^9$-THC, and CBN were dissolved in water at 10 ppm, 25 ppm, 50 ppm, 100 ppm, and 250 ppm to prepare standard solutions, respectively, which were used to construct calibration curves. An elution solvent A and an elution solvent B used in ultra-performance liquid chromatography (UPLC) were water and acetonitrile, respectively, and each was pumped using two pumps. 3 μl of the standard aqueous solution was injected into a reverse-phase column for analysis (Phenomenex Luna Omega 1.6μ Polar C18, 150 mm×2.1 mm) using a syringe, and an elution solvent consisting of 70% by volume of A and 30% by volume of B was applied at a flow rate of 0.3 mL/min. Thereafter, % volume of the elution solvent B were gradually changed to 100% (20 min), 100% (23 min), and 30% (26 min). After the above procedures, each ingredient isolated from the column was analyzed by UV spectrum.

(2) Experimental Results

As a result of the experiments, each ingredient isolated from the column was analyzed by UPLC analysis of the cannabis leaf extracts, and peaks of FIGS. 2 to 36 were obtained by the analysis results of UPLC chromatograms.

Figure 2:
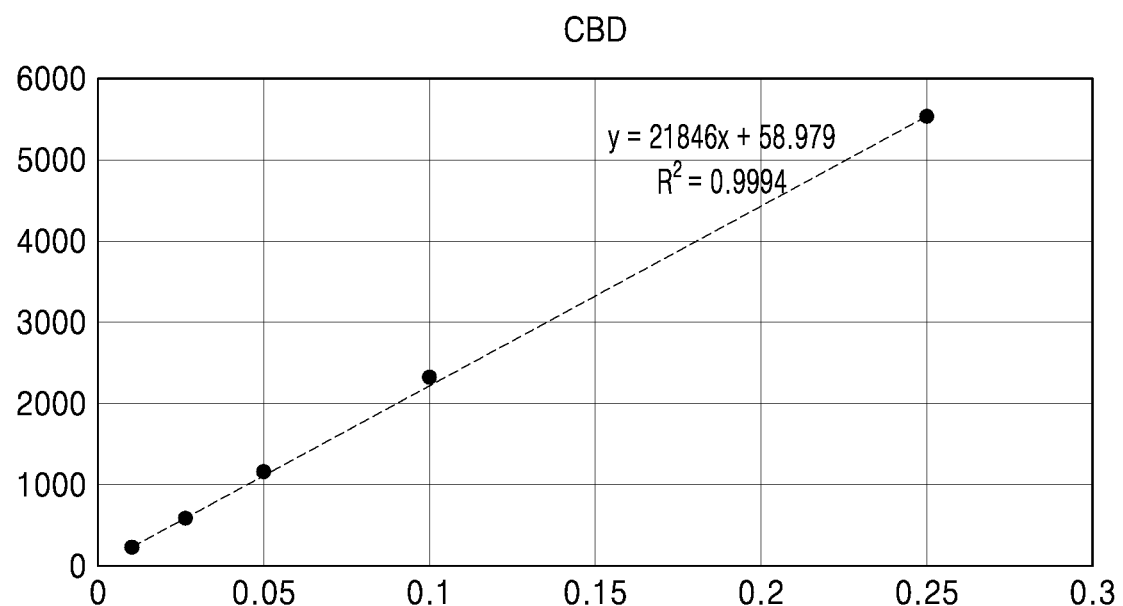
FIG. 2 shows a calibration curve constructed by analyzing CBD according to concentrations.

FIG. 2 shows a calibration curve constructed by analyzing CBD according to concentrations.

Figure 3:
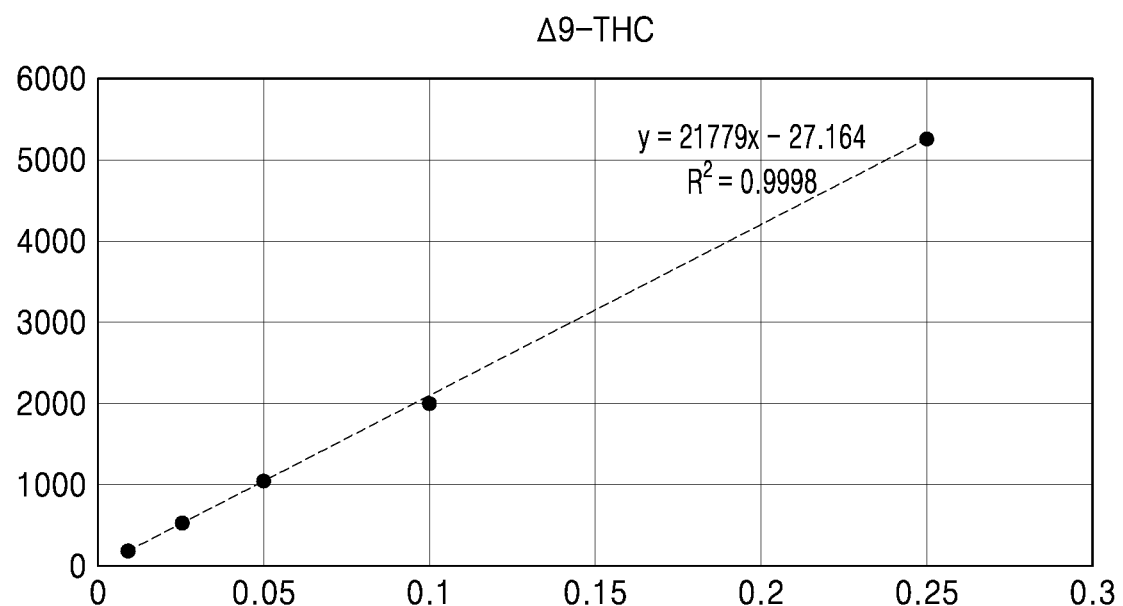
FIG. 3 shows a calibration curve constructed by analyzing $\Delta^9$-THC according to concentrations.

FIG. 3 shows a calibration curve constructed by analyzing $\Delta^9$-THC according to concentrations.

Figure 4:
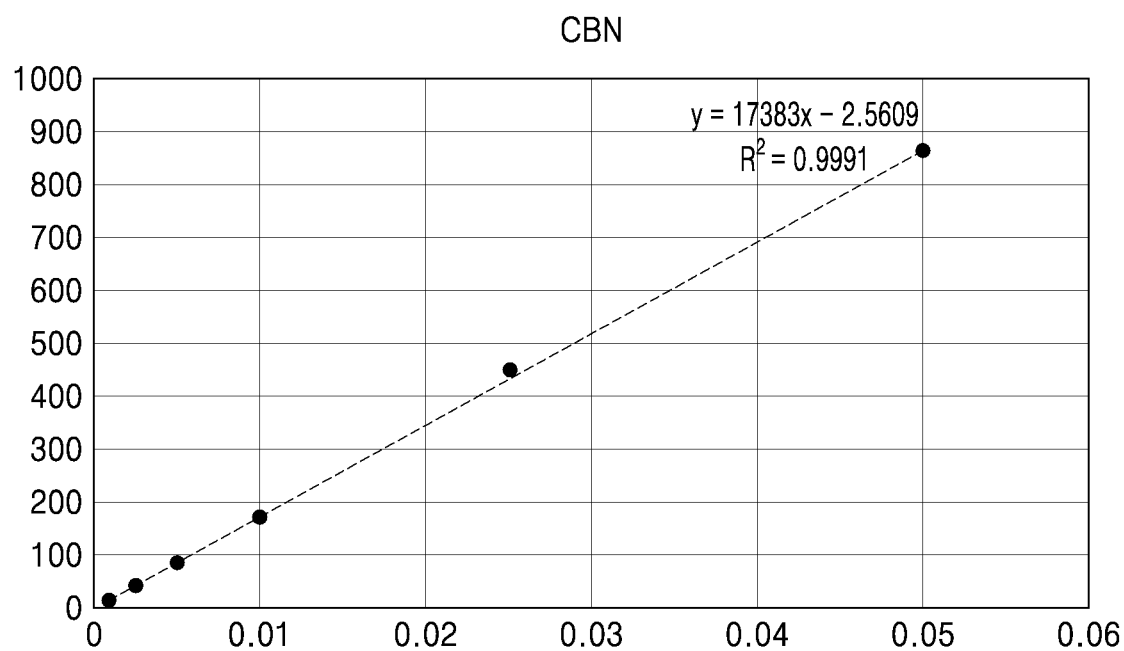
FIG. 4 shows a calibration curve constructed by analyzing CBN according to concentrations.

FIG. 4 shows a calibration curve constructed by analyzing CBN according to concentrations.

Figure 5:
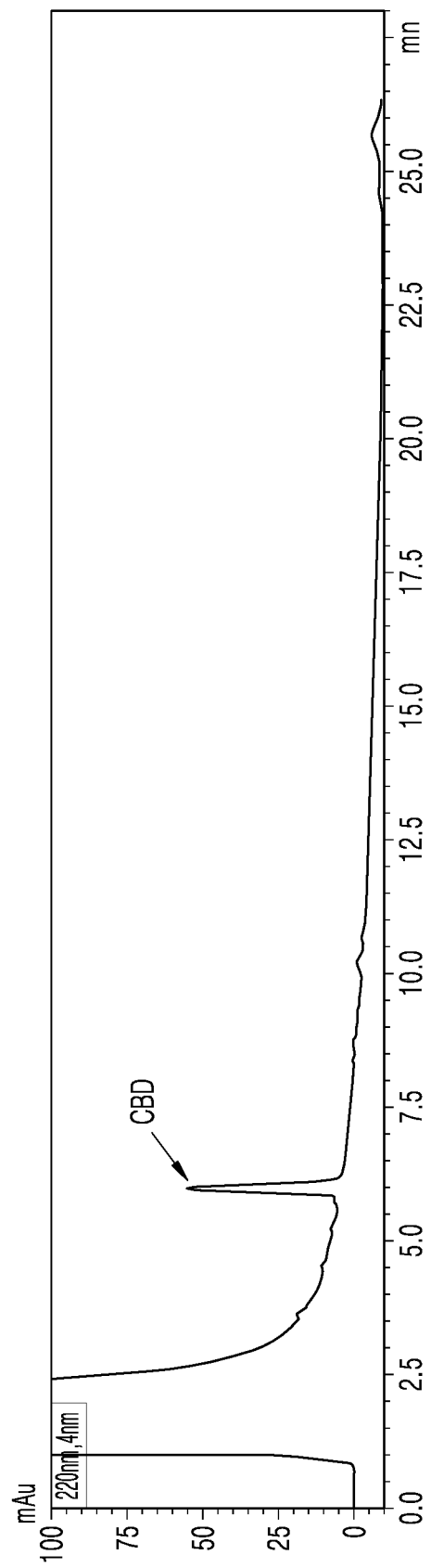
FIG. 5 shows a UPLC chromatogram for analyzing cannabinoid ingredients in an extract A of a raw material dry cannabis leaf.

FIG. 5 shows a UPLC chromatogram for analyzing cannabinoid ingredients in an extract A of a raw material dry cannabis leaf.

Figure 6:
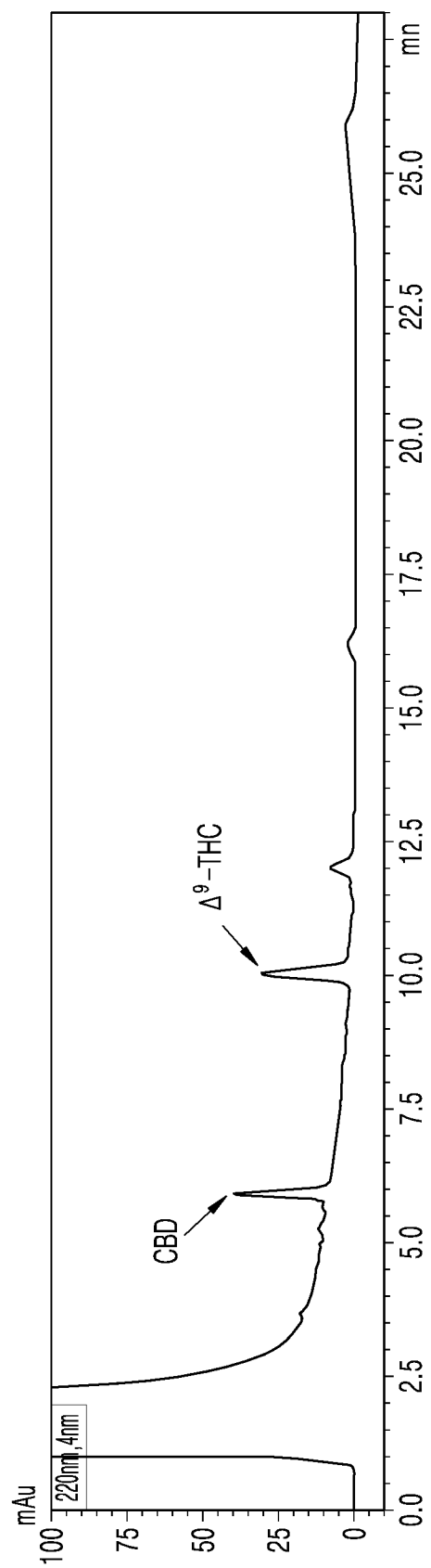
FIG. 6 shows a UPLC chromatogram for analyzing cannabinoid ingredients in an extract B of a raw material dry cannabis leaf.

FIG. 6 shows a UPLC chromatogram for analyzing cannabinoid ingredients in an extract B of a raw material dry cannabis leaf.

Figure 7:
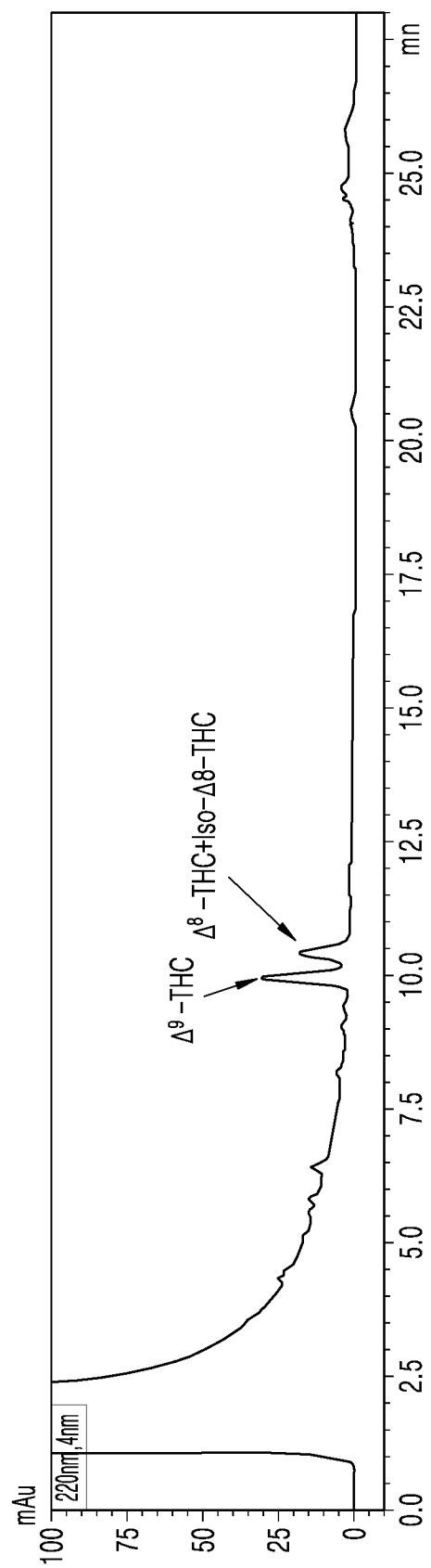
FIG. 7 shows a UPLC chromatogram for analyzing cannabinoid ingredients in an extract C of a raw material dry cannabis leaf.

FIG. 7 shows a UPLC chromatogram for analyzing cannabinoid ingredients in an extract C of a raw material dry cannabis leaf.

Figure 8:
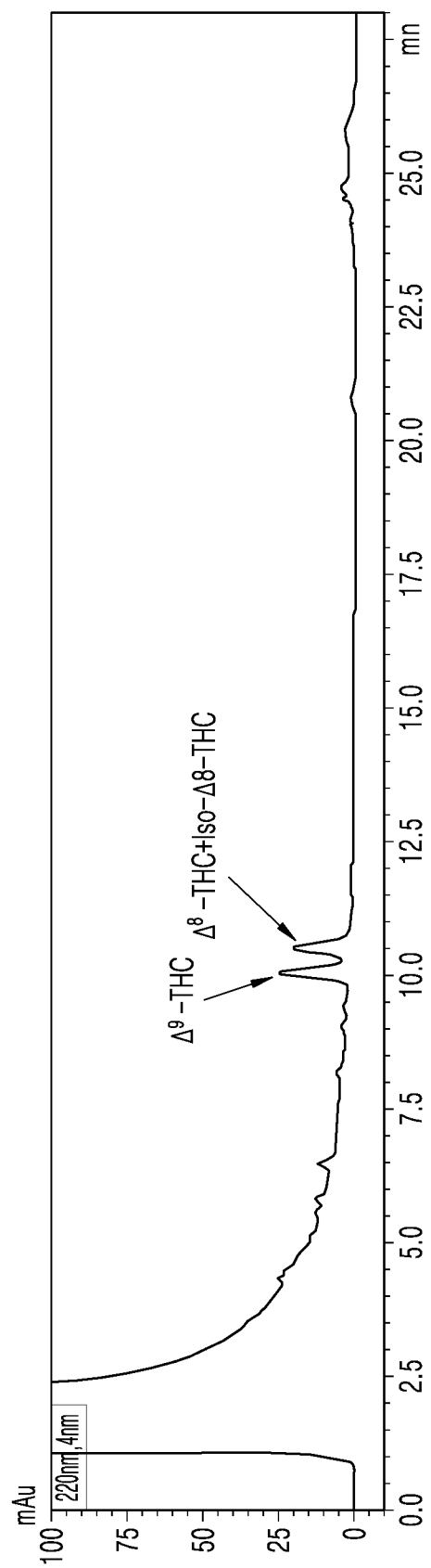
FIG. 8 shows a UPLC chromatogram for analyzing cannabinoid ingredients in a processed product obtained by microwave-irradiation in a batch manner at 80° C. for 30 minutes while adding 20 equivalent weights of PTSA, relative to CBD, to a 200 ppm solution of the extract A of cannabis leaves in ethanol.

FIG. 8 shows a UPLC chromatogram for analyzing cannabinoid ingredients in a processed product obtained by microwave-irradiation in a batch manner at 80° C. for 30 minutes while adding 20 equivalent weights of PTSA, relative to CBD, to a 200 ppm solution of the extract A of cannabis leaves in ethanol.

Figure 9:
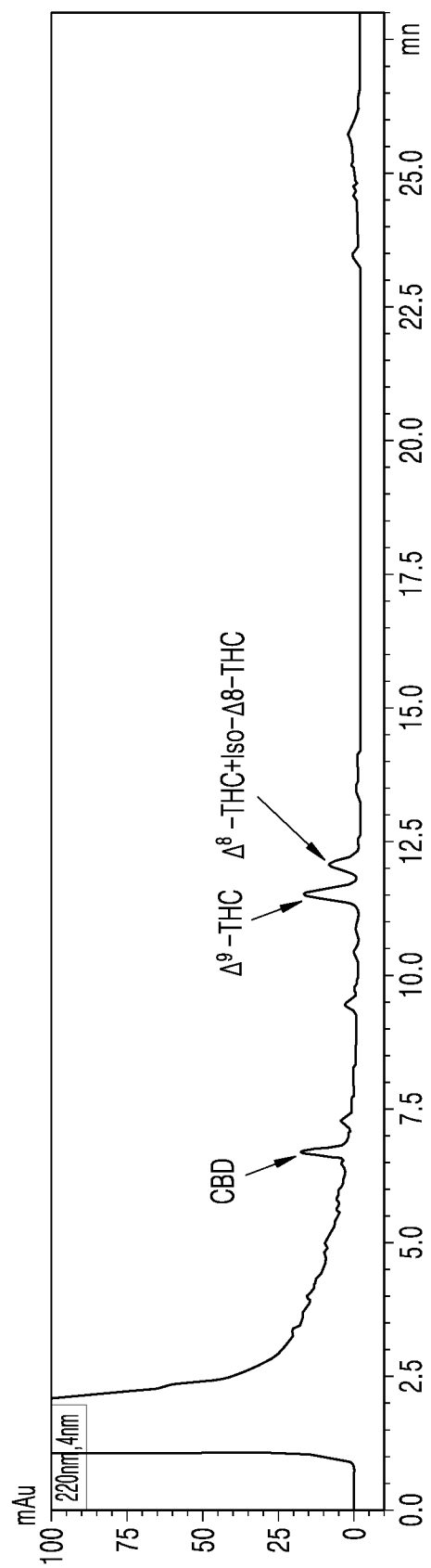
FIG. 9 shows a UPLC chromatogram for analyzing cannabinoid ingredients in a processed product obtained by microwave-irradiation in a batch manner at 80° C. for 60 minutes while adding 20 equivalent weights of PTSA, relative to CBD, to a 200 ppm solution of the extract A of cannabis leaves in ethanol.

FIG. 9 shows a UPLC chromatogram for analyzing cannabinoid ingredients in a processed product obtained by microwave-irradiation in a batch manner at 80° C. for 60 minutes while adding 20 equivalent weights of PTSA, relative to CBD, to a 200 ppm solution of the extract A of cannabis leaves in ethanol.

Figure 10:
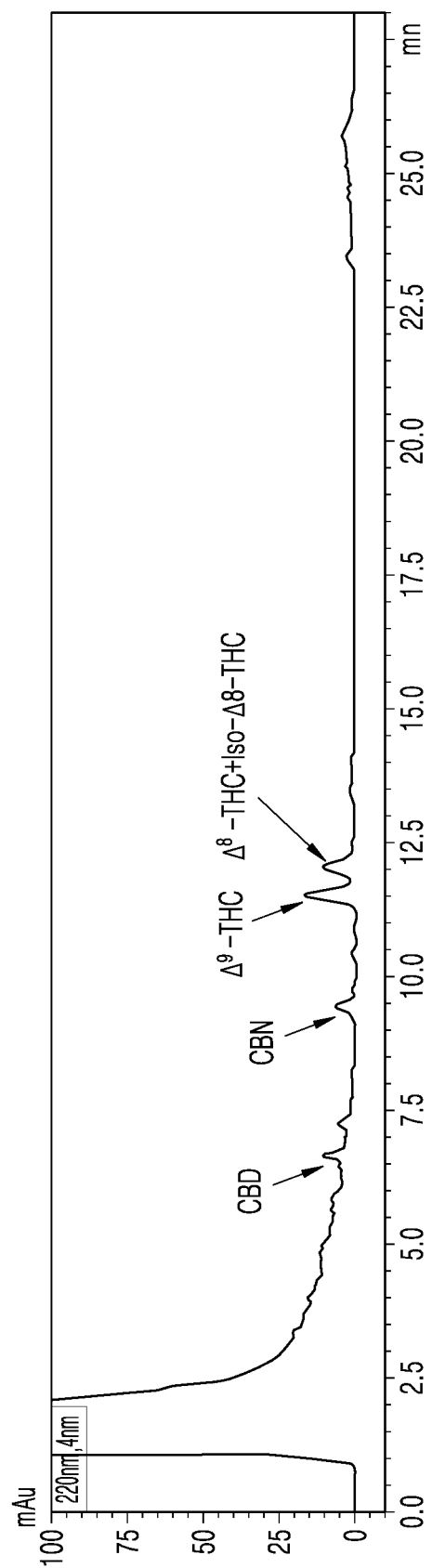
FIG. 10 shows a UPLC chromatogram for analyzing cannabinoid ingredients in a processed product obtained by microwave-irradiation for 40 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 60° C. at a flow rate of 0.25 mL/min.

FIG. 10 shows a UPLC chromatogram for analyzing cannabinoid ingredients in a processed product obtained by microwave-irradiation for 40 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 60° C. at a flow rate of 0.25 mL/min.

Figure 11:
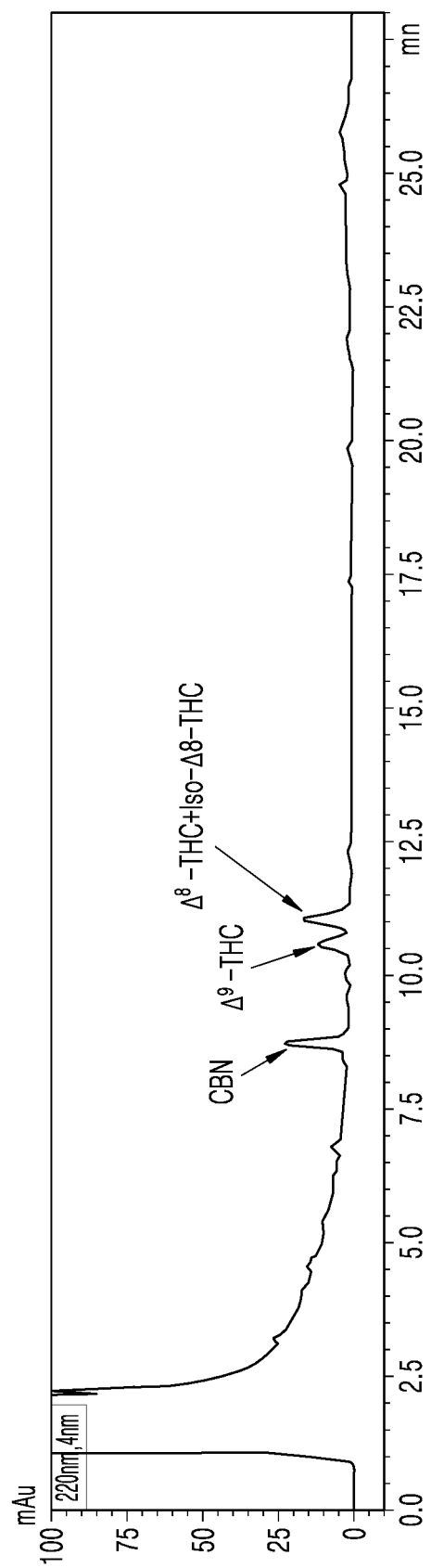
FIG. 11 shows a UPLC chromatogram for analyzing cannabinoid ingredients in a processed product obtained by microwave-irradiation for 60 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 60° C. at a flow rate of 0.017 mL/min.

FIG. 11 shows a UPLC chromatogram for analyzing cannabinoid ingredients in a processed product obtained by microwave-irradiation for 60 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 60° C. at a flow rate of 0.017 mL/min.

Figure 12:
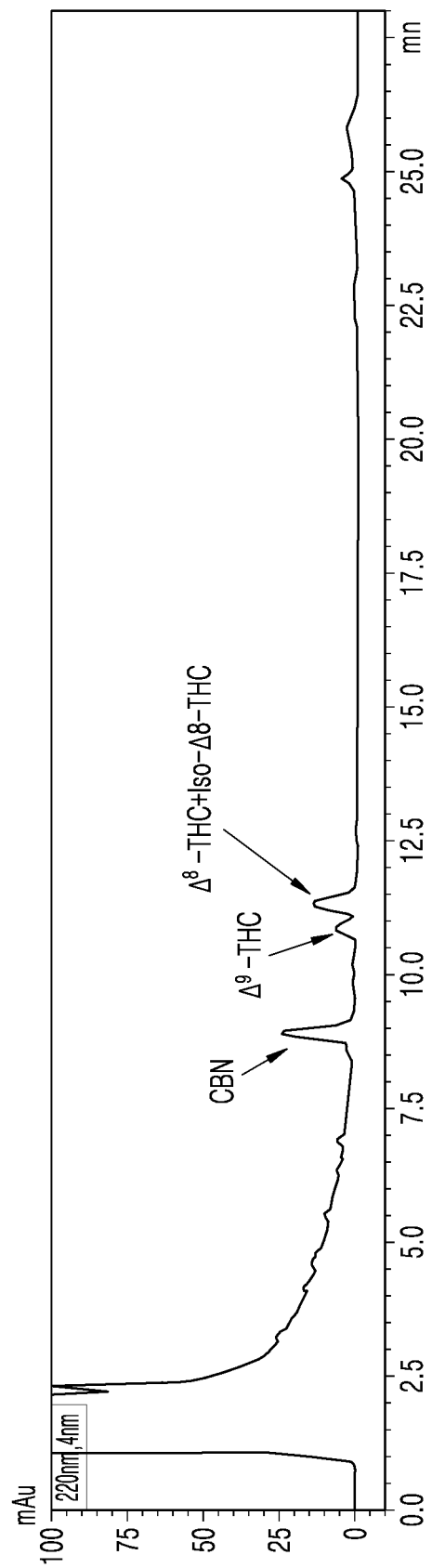
FIG. 12 shows a UPLC chromatogram for analyzing cannabinoid ingredients in a processed product obtained by microwave-irradiation for 40 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 70° C. at a flow rate of 0.025 mL/min.

FIG. 12 shows a UPLC chromatogram for analyzing cannabinoid ingredients in a processed product obtained by microwave-irradiation for 40 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 70° C. at a flow rate of 0.025 mL/min.

Figure 13:
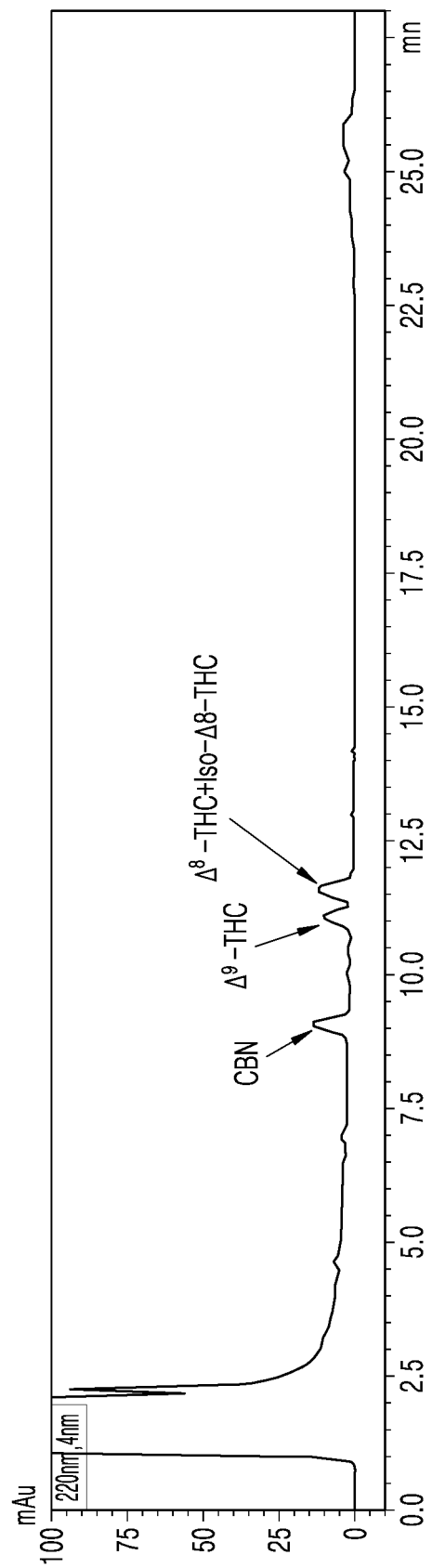
FIG. 13 shows a UPLC chromatogram for analyzing cannabinoid ingredients in a processed product obtained by microwave-irradiation for 60 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 70° C. at a flow rate of 0.017 mL/min.

FIG. 13 shows a UPLC chromatogram for analyzing cannabinoid ingredients in a processed product obtained by microwave-irradiation for 60 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 70° C. at a flow rate of 0.017 mL/min.

Figure 14:
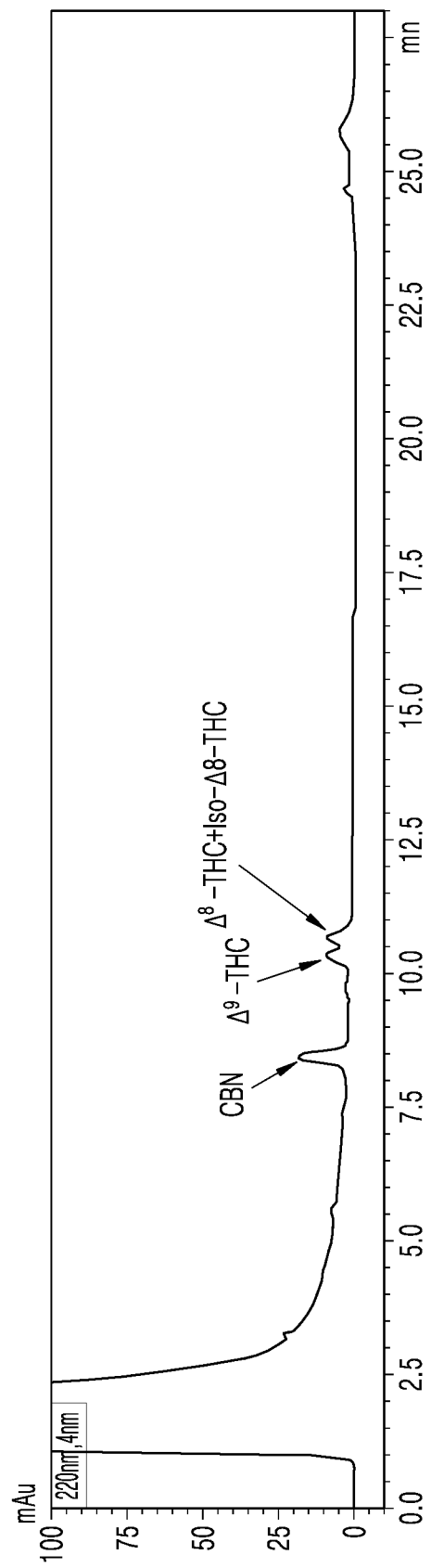
FIG. 14 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 80° C. at a flow rate of 0.050 mL/min.

FIG. 14 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 80° C. at a flow rate of 0.050 mL/min.

Figure 15:
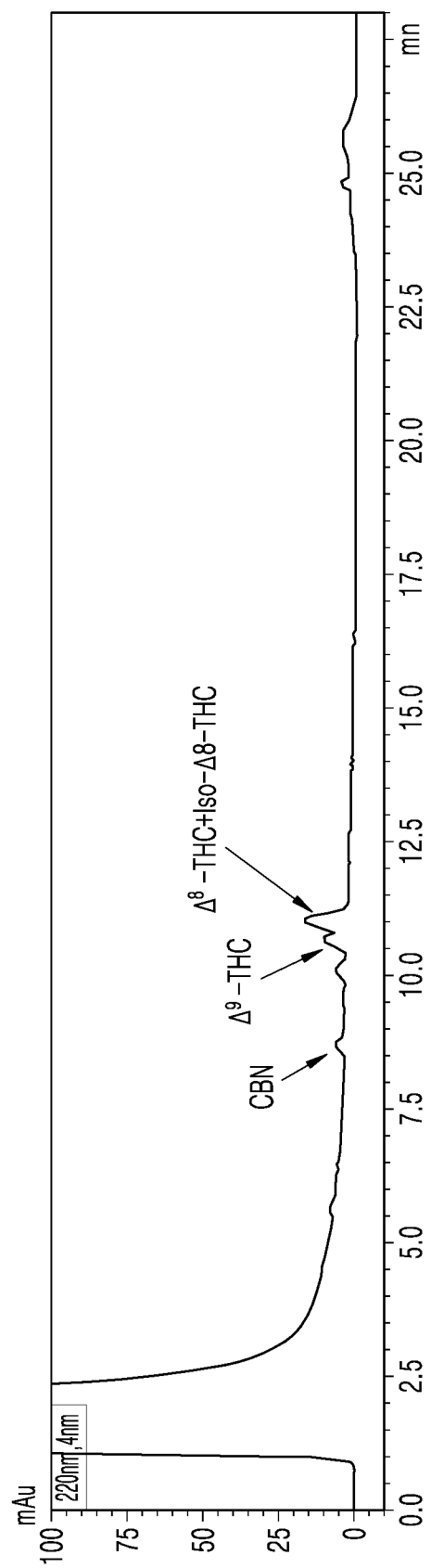
FIG. 15 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 90° C. at a flow rate of 0.050 mL/min.

FIG. 15 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 90° C. at a flow rate of 0.050 mL/min.

Figure 16:
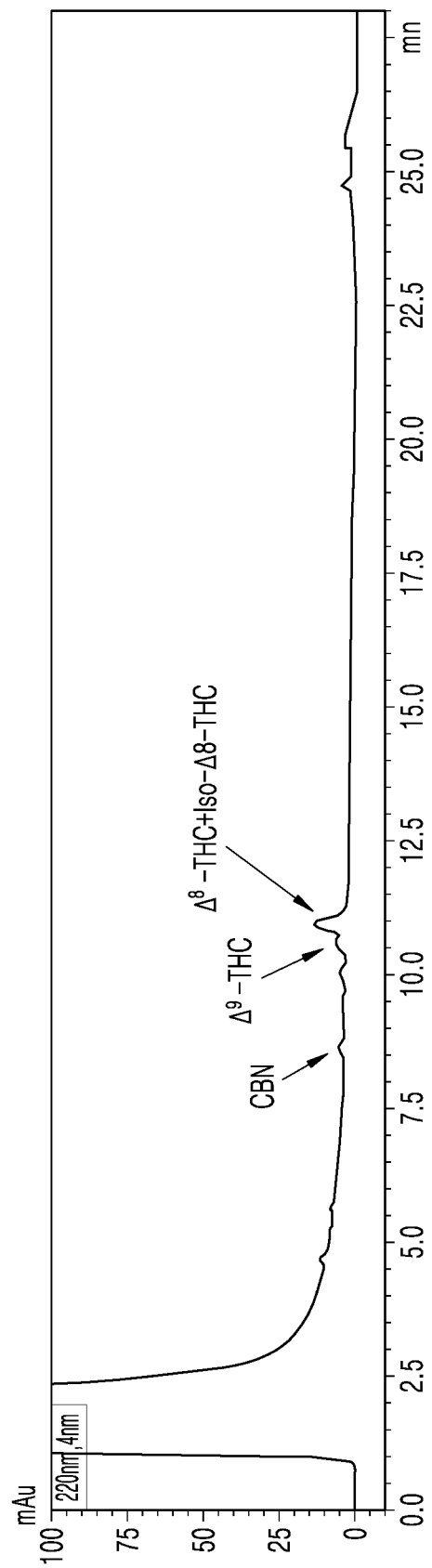
FIG. 16 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.050 mL/min.

FIG. 16 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.050 mL/min.

Figure 17:
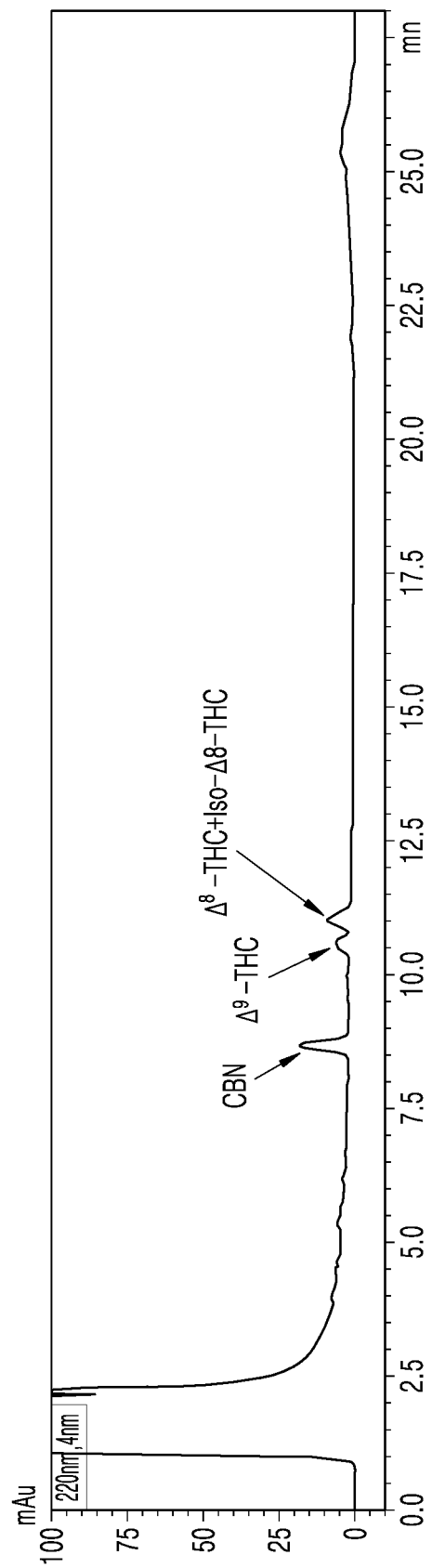
FIG. 17 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 110° C. at a flow rate of 0.050 mL/min.

FIG. 17 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 110° C. at a flow rate of 0.050 mL/min.

Figure 18:
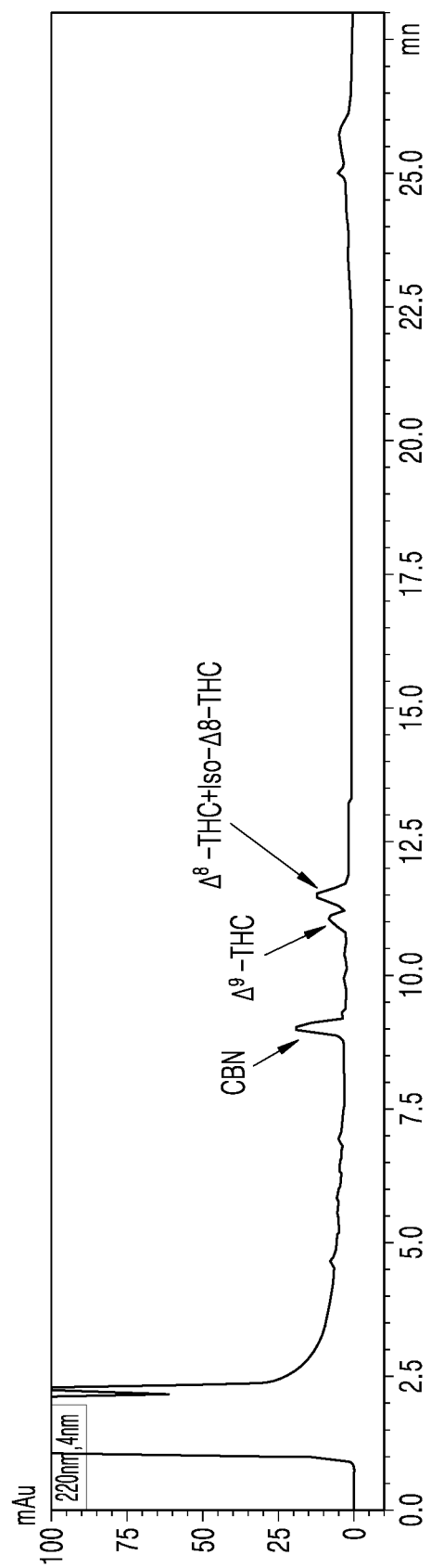
FIG. 18 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 120° C. at a flow rate of 0.050 mL/min.

FIG. 18 shows a UPLC chromatogram for analyzing cannabinoid ingredients in a processed product obtained by microwave-irradiation for 20 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 120° C. at a flow rate of 0.050 mL/min.

Figure 19:
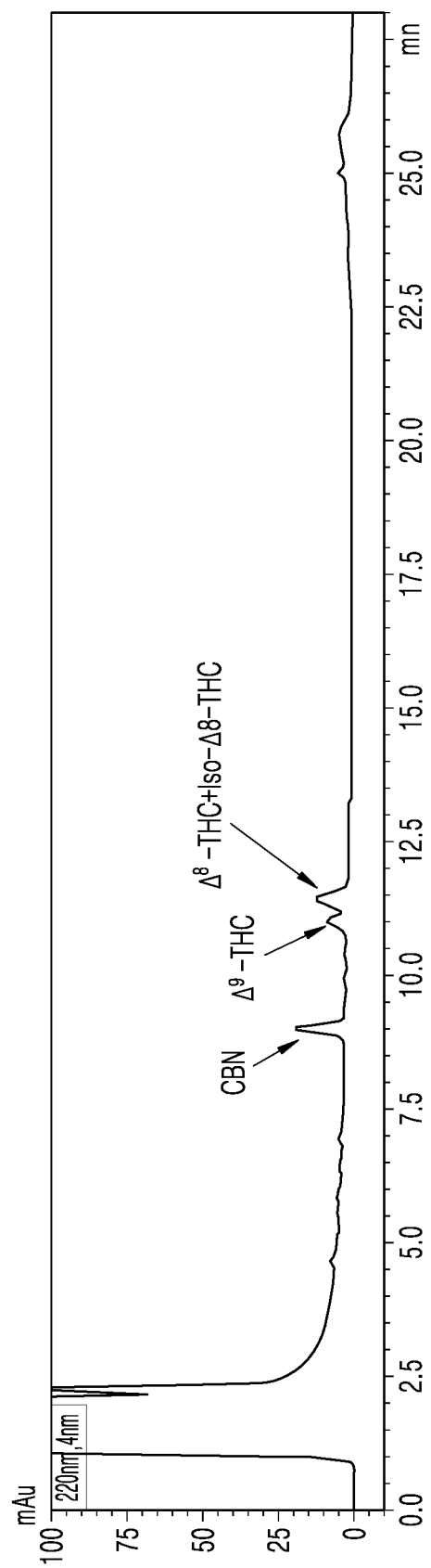
FIG. 19 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 19 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

Figure 20:
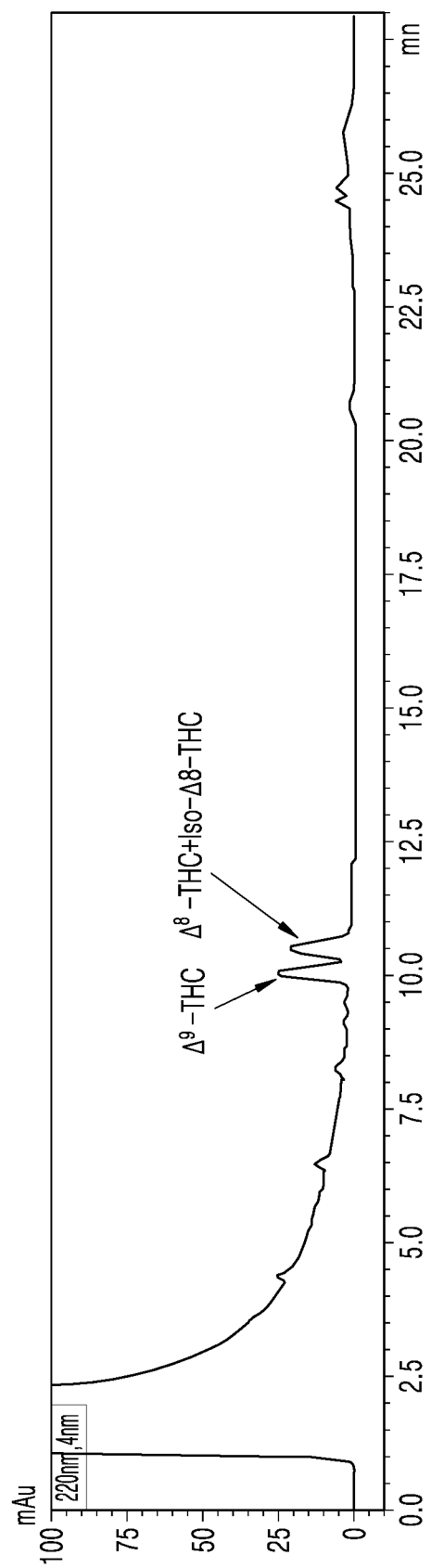
FIG. 20 shows a UPLC chromatogram for analyzing cannabinoid ingredients in a processed product obtained by microwave-irradiation for 40 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.025 mL/min.

FIG. 20 shows a UPLC chromatogram for analyzing cannabinoid ingredients in a processed product obtained by microwave-irradiation for 40 minutes while adding 20 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.025 mL/min.

Figure 21:
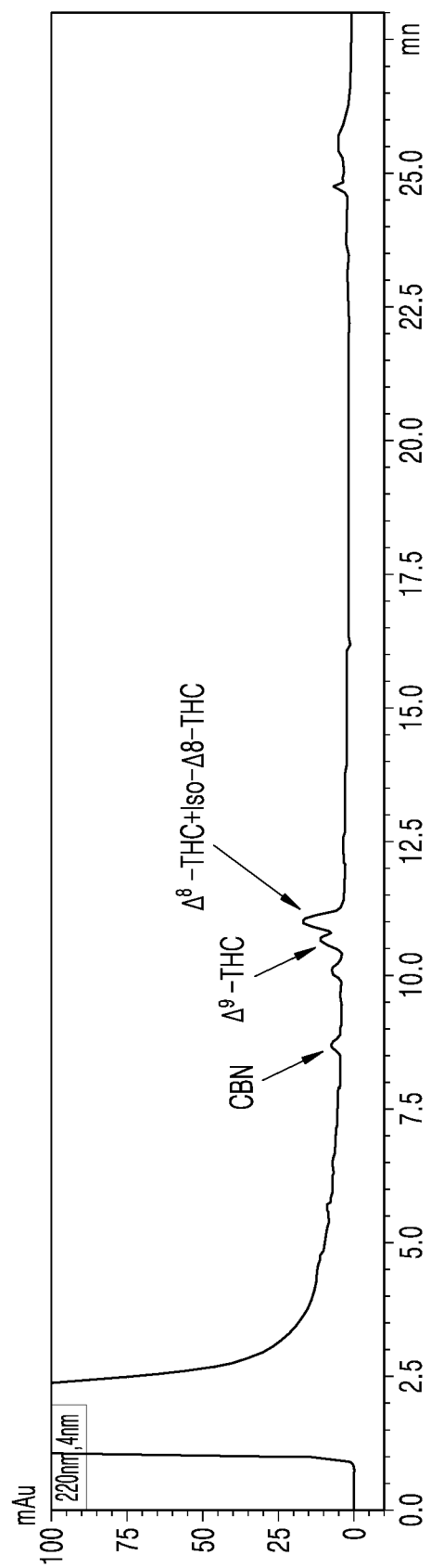
FIG. 21 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in isopropanol (IPA) and applying the solution to a tube with a volume of 1.0 mL through a liquid-feeding pump at 100° C. at a flow rate of 0.033 mL/min.

FIG. 21 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in isopropanol (IPA) and applying the solution to a tube with a volume of 1.0 mL through a liquid-feeding pump at 100° C. at a flow rate of 0.033 mL/min.

Figure 22:
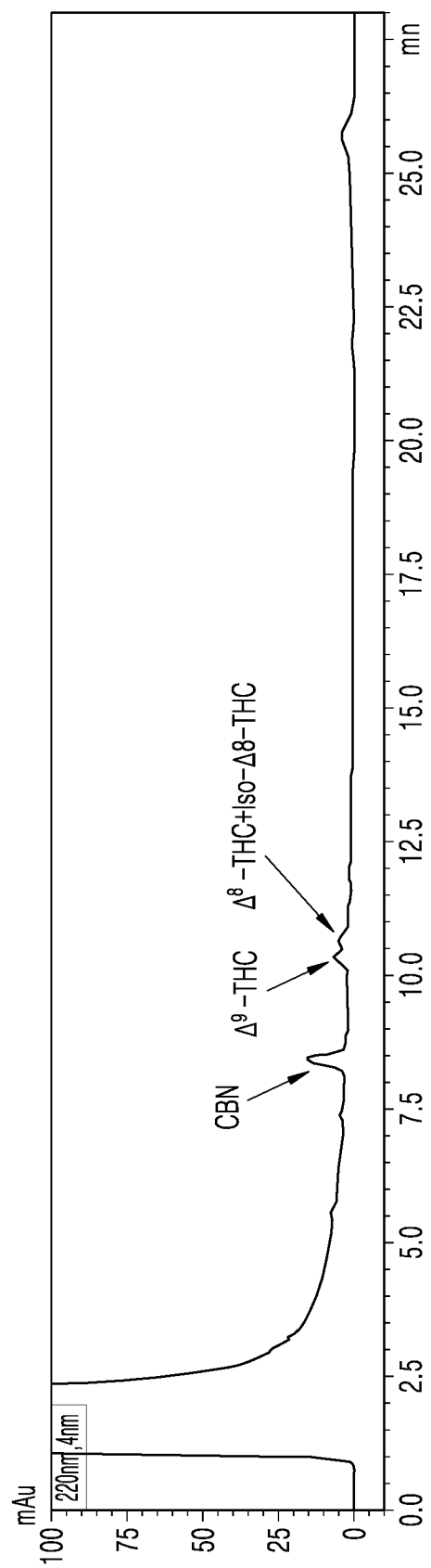
FIG. 22 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in ethyl acetate (EtOAc) and applying the solution to a tube with a volume of 1.0 mL through a liquid-feeding pump at 100° C. at a flow rate of 0.033 mL/min.

FIG. 22 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in ethyl acetate (EtOAc) and applying the solution to a tube with a volume of 1.0 mL through a liquid-feeding pump at 100° C. at a flow rate of 0.033 mL/min.

Figure 23:
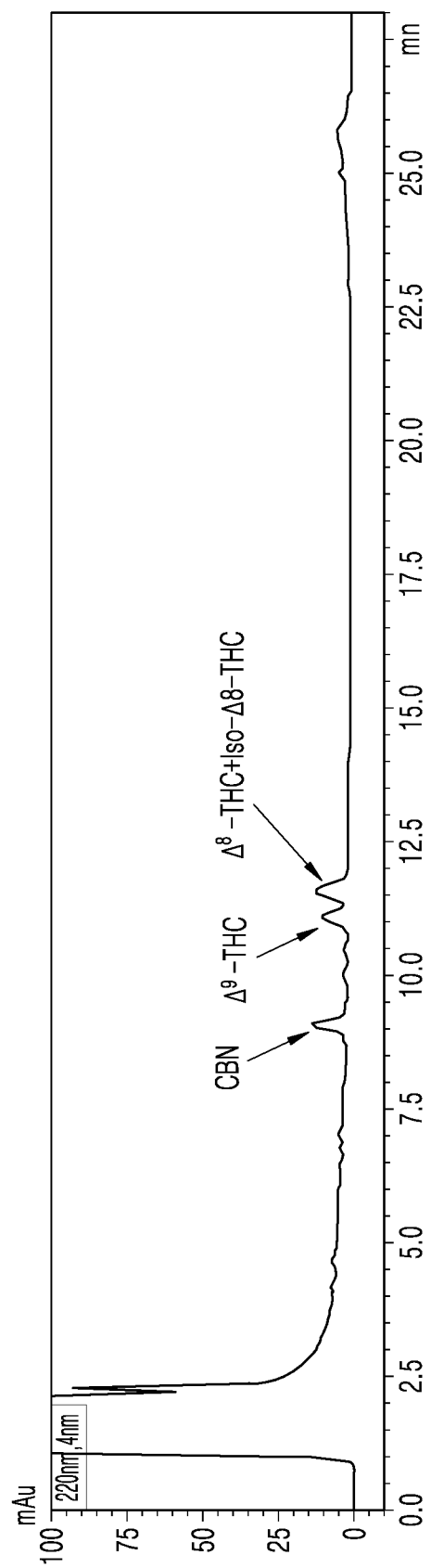
FIG. 23 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in butanol (BuOH) and applying the solution to a tube with a volume of 1.0 mL through a liquid-feeding pump at 100° C. at a flow rate of 0.033 mL/min.

FIG. 23 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in butanol (BuOH) and applying the solution to a tube with a volume of 1.0 mL through a liquid-feeding pump at 100° C. at a flow rate of 0.033 mL/min.

Figure 24:
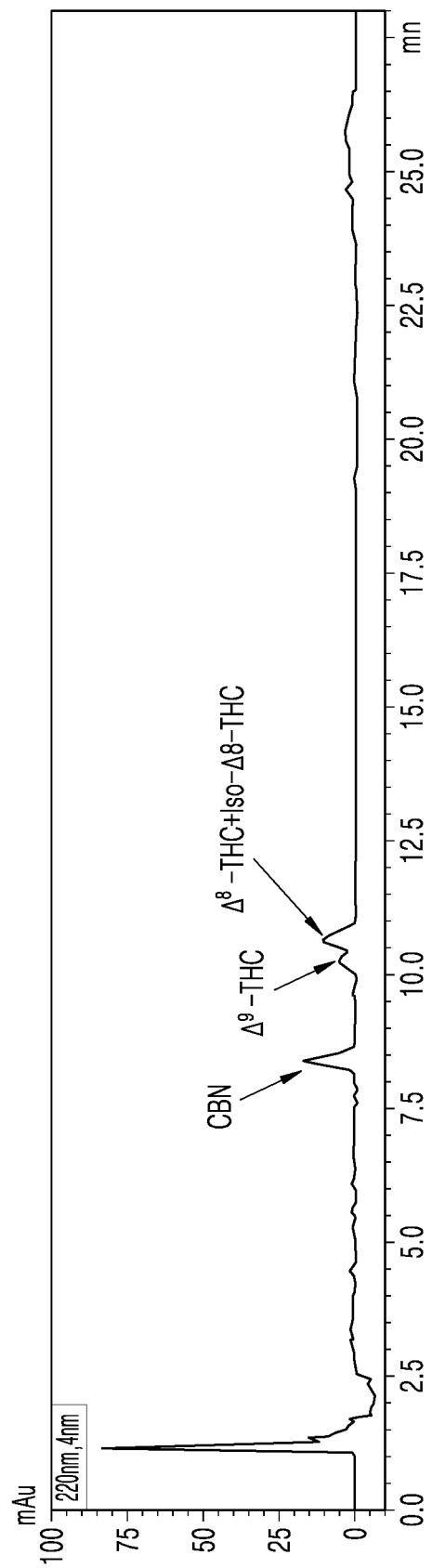
FIG. 24 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in a 70% ethanol (EtOH) aqueous solution and applying the solution to a tube with a volume of 1.0 mL through a liquid-feeding pump at 100° C. at a flow rate of 0.033 mL/min.

FIG. 24 shows a UPLC chromatogram for analyzing cannabinoid ingredients in a processed product obtained by microwave-irradiation for 30 minutes while adding 20 equivalent weights of PTSA, relative to CBD, to a 200 ppm solution of the extract A of cannabis leaves in a 70% ethanol (EtOH) aqueous solution and applying the solution to a tube with a volume of 1.0 mL through a liquid-feeding pump at 100° C. at a flow rate of 0.033 mL/min.

FIG. 25 shows a UPLC chromatogram for analyzing cannabinoid ingredients in a processed product obtained by microwave-irradiation for 30 minutes while adding 20 equivalent weights of sulfuric acid, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 26 shows a UPLC chromatogram for analyzing cannabinoid ingredients in a processed product obtained by microwave-irradiation for 30 minutes while adding 20 equivalent weights of camphorsulfonic acid (CSA), relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 27 shows a UPLC chromatogram for analyzing cannabinoid ingredients in a processed product obtained by microwave-irradiation for 30 minutes while adding 20 equivalent weights of methanesulfonic acid (MSA), relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 28 shows a UPLC chromatogram for analyzing cannabinoid ingredients in a processed product obtained by microwave-irradiation for 30 minutes while adding 10 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 29 shows a UPLC chromatogram for analyzing cannabinoid ingredients in a processed product obtained by microwave-irradiation for 30 minutes while adding 30 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 30 shows a UPLC chromatogram for analyzing cannabinoid ingredients in a processed product obtained by microwave-irradiation for 30 minutes while adding 40 equivalent weights of PTSA, relative to CBD, to a 200 ppm solution of the extract A of cannabis leaves in ethanol and applying the solution to a tube with a volume of 1.0 mL through a liquid-feeding pump at 100° C. at a flow rate of 0.033 mL/min.

FIG. 31 shows a UPLC chromatogram for analyzing cannabinoid ingredients in a processed product obtained by microwave-irradiation for 10 minutes while adding 20 equivalent weights of PTSA, relative to the total weight of CBD and $\Delta^9$-THC, to a 200 ppm solution of the extract B of cannabis leaves in ethanol and applying the solution to a tube with a volume of 1.0 mL through a liquid-feeding pump at 80° C. at a flow rate of 0.10 mL/min.

FIG. 32 shows a UPLC chromatogram for analyzing cannabinoid ingredients in a processed product obtained by microwave-irradiation for 10 minutes while adding 20 equivalent weights of PTSA, relative to the total weight of CBD and $\Delta^9$-THC, to a 200 ppm solution of the extract B of cannabis leaves in ethanol and applying the solution to a tube with a volume of 1.0 mL through a liquid-feeding pump at 80° C. at a flow rate of 0.050 mL/min.

FIG. 33 shows a UPLC chromatogram for analyzing cannabinoid ingredients in a processed product obtained by microwave-irradiation for 30 minutes while adding 20 equivalent weights of PTSA, relative to the total weight of CBD and $\Delta^9$-THC, to a 200 ppm solution of the extract B of cannabis leaves in ethanol and applying the solution to a tube with a volume of 1.0 mL through a liquid-feeding pump at 80° C. at a flow rate of 0.033 mL/min.

FIG. 34 shows a UPLC chromatogram for analyzing cannabinoid ingredients in a processed product obtained by microwave-irradiation for 10 minutes while adding 20 equivalent weights of PTSA, relative to the total weight of $\Delta^9$-THC, to a 200 ppm solution of the extract C of cannabis leaves in ethanol and applying the solution to a tube with a volume of 1.0 mL through a liquid-feeding pump at 80° C. at a flow rate of 0.100 mL/min.

FIG. 35 shows a UPLC chromatogram for analyzing cannabinoid ingredients in a processed product obtained by microwave-irradiation for 20 minutes while adding 20 equivalent weights of PTSA, relative to the total weight of $\Delta^9$-THC, to a 200 ppm solution of the extract C of cannabis leaves in ethanol and applying the solution to a tube with a volume of 1.0 mL through a liquid-feeding pump at 80° C. at a flow rate of 0.050 mL/min.

FIG. 36 shows a UPLC chromatogram for analyzing cannabinoid ingredients in a processed product obtained by microwave-irradiation for 30 minutes while adding 20 equivalent weights of PTSA, relative to the total weight of $\Delta^9$-THC, to a 200 ppm solution of the extract C of cannabis leaves in ethanol and applying the solution to a tube with a volume of 1.0 mL through a liquid-feeding pump at 80° C. at a flow rate of 0.033 mL/min.

First, the results of calculating the contents of CBD, $\Delta^9$-THC, and CBN in UPLC chromatograms obtained by continuous microwave processing of the cannabis extracts at different temperatures for different times are summarized in Table 1.

TABLE 1

| Item | Temperature (° C.)-time (min) | Acid-equivalent weight (eq) | CBD (mg) | $\Delta^9$-THC (mg) | CBN (mg) | CBN yield* (%) |
|---|---|---|---|---|---|---|
| Extract A | — | | 62.2 | n.d | n.d | 0 |
| Control group 1 | 80-30 | PTSA-20 | n.d | 39.2 | n.d | 0 |
| Control group 2 | 80-60 | PTSA-20 | n.d | 34.4 | n.d | 0 |
| Experimental group 1 | 60-40 | PTSA-20 | 12.0 | 27.8 | 4.2 | 6.8 |
| Experimental group 2 | 60-60 | PTSA-20 | 4.4 | 25.4 | 8.7 | 14.2 |
| Experimental group 3 | 70-40 | PTSA-20 | n.d | 14.6 | 25.0 | 40.7 |
| Experimental group 4 | 70-60 | PTSA-20 | n.d | 10.0 | 30.2 | 49.2 |
| Experimental group 5 | 80-20 | PTSA-20 | n.d | 22.0 | 26.3 | 42.8 |
| Experimental group 6 | 90-20 | PTSA-20 | n.d | 15.3 | 33.4 | 54.4 |
| Experimental group 7 | 100-20 | PTSA-20 | n.d | 16.0 | 35.9 | 58.5 |
| Experimental group 8 | 110-20 | PTSA-20 | n.d | 18.4 | 6.6 | 10.7 |
| Experimental group 9 | 120-20 | PTSA-20 | n.d | 9.4 | 3.3 | 5.4 |
| Experimental group 10 | 100-30 | PTSA-20 | n.d | 15.2 | 37.1 | 60.4 |
| Experimental group 11 | 100-40 | PTSA-20 | n.d | 11.4 | 36.0 | 58.6 |

*CBN yield=(CBN mg/61.4 mg(Theoretical CBN amount at 100% conversion)×100**n.d=not detected Table 1 shows CBD, $\Delta^9$-THC, and CBN contents expressed in mg per 1 g of the extract, after dissolving the extract A of dry cannabis leaves in ethanol at a concentration of 200 ppm, adding 20 equivalent weights of PTSA, relative to CBD, and processing by continuous microwave irradiation. It was confirmed that $\Delta^8$-THC and cannabicitran were produced as by-products during processing. However, they were inseparable mixtures, and thus the exact production amounts thereof were not calculated. In the initial cannabis leaf extract A during processing, cannabinoids were found to include only 62.2 mg of CBD per g, and $\Delta^9$-THC and CBN were not found.

Prior to this experiment, in order to compare the batch method and the flow method, an experiment was performed using a batch-type microwave reactor at 80° C. for 30 minutes (control group 1) and 60 minutes (control group 2). As a result, the production of $\Delta^9$-THC through cyclization of CBD was found, but the conversion to CBN through aromatization was not found. However, when reaction was allowed for 40 minutes at 60° C. in the continuous manner, it was confirmed that CBD remained, but the final product CBN was produced via the intermediate $\Delta^9$-THC. Thereafter, experiments were performed at 60° C. to 120° C. at 10° C. intervals, and measurements were performed between 10 minutes and 60 minutes to examine the influence of time on temperature. First, when the experiment was performed for up to 60 minutes at 60° C., the raw material CBD remained, and the largest amount of the intermediate $\Delta^9$-THC was observed. When the temperature was raised to 70° C., CBD was exhausted and CBN was increased. Next, the time was fixed at 20 minutes, and the experiment was performed while raising the temperature from 80° C. to 120° C. As a result, the best result was obtained at 100° C. and 20 minutes. Finally, it was confirmed that when the experiment was performed at 100° C. by increasing the time, CBD was converted to CBN with the highest yield of 60.4% in 30 minutes.

Further, the results of calculating the contents of CBD, $\Delta^9$-THC, and CBN in UPLC chromatograms obtained by continuous microwave processing of the cannabis extracts in different solvents are summarized in Table 2.

TABLE 2

| Item | Solvent | Temperature (° C.)-time (min) | Acid-equivalent weight (eq) | CBD (mg) | $\Delta^9$-THC (mg) | CBN (mg) | CBN yield* (%) |
|---|---|---|---|---|---|---|---|
| Extract A | — | | | 62.2 | 0 | 0 | 0% |
| Experimental group 10 | EtOH | 100-30 | PTSA-20 | n.d | 15.2 | 37.1 | 60.4% |
| Experimental group 11 | IPA | 100-30 | PTSA-20 | n.d | 14.9 | 16.5 | 26.9% |
| Experimental group 12 | EtOAc | 100-30 | PTSA-20 | n.d | 9.8 | 23.5 | 38.3% |
| Experimental group 13 | BuOH | 100-30 | PTSA-20 | n.d | 15.8 | 28.3 | 46.1% |
| Experimental group 14 | 70% EtOH | 100-30 | PTSA-20 | n.d | 17.0 | 31.2 | 50.8% |

*CBN yield=(CBN mg/61.4 mg(Theoretical CBN amount at 100% conversion)×100**n.d=not detected Table 2 shows CBD, $\Delta^9$-THC, and CBN contents expressed in mg per 1 g of the extract, after dissolving the extract A of dry cannabis leaves in each solvent at a concentration of 200 ppm, adding 20 equivalent weights of PTSA, relative to CBD, and processing by continuous microwave irradiation under conditions of experimental group 10 (100° C., 30 minutes) showing the highest CBN yield in Table 1. As a result, when the solvent isopropanol (IPA), ethyl acetate (EtOAc), butanol (BuOH), and 70% EtOH aqueous solution were used, the CBN content was 26.9%, 38.3%, 46.1%, and 50.8%, respectively. The yield was lower than that of ethanol, but CBN was obtained.

Further, the results of calculating the contents of CBD, $\Delta^9$-THC, and CBN in UPLC chromatograms obtained by continuous microwave processing of the cannabis extracts with different acids and equivalent weights are summarized in Table 3.

TABLE 3

| Item | Temperature (° C.)-time (min) | Acid-equivalent weight (eq) | CBD (mg) | $\Delta^9$-THC (mg) | CBN (mg) | CBN yield* (%) |
|---|---|---|---|---|---|---|
| Extract A | | | 62.2 | 0 | 0 | 0 |
| Experimental group 10 | 100-30 | PTSA-20 | n.d | 15.2 | 37.1 | 60.4 |
| Experimental group 16 | 100-30 | Sulfuric acid-20 | n.d | 7.6 | 4.8 | 7.8 |
| Experimental group 17 | 100-30 | CSA-20 | n.d | 9.1 | 32.2 | 52.4 |
| Experimental group 18 | 100-30 | MSA-20 | n.d | 20.0 | 12.3 | 20.0 |
| Experimental group 19 | 100-30 | PTSA-10 | n.d | 5.3 | 32.1 | 52.3 |
| Experimental group 20 | 100-30 | PTSA-30 | n.d | 15.5 | 36.5 | 59.4 |

TABLE 3-continued

| Item | Temperature (° C.)-time (min) | Acid-equivalent weight (eq) | CBD (mg) | $\Delta^9$-THC (mg) | CBN (mg) | CBN yield* (%) |
|---|---|---|---|---|---|---|
| Experimental group 21 | 100-30 | PTSA-40 | n.d | 16.3 | 37.2 | 60.6 |

*CBN yield=(CBN mg/61.4 mg(Theoretical CBN amount at 100% conversion)×100**n.d=not detected Table 3 shows CBD, $\Delta^9$-THC, and CBN contents expressed in mg per 1 g of the extract, after dissolving the extract A of dry cannabis leaves in each solvent at a concentration of 200 ppm, and processing by continuous microwave irradiation with varying the kind of acid and the equivalent weight under conditions of experimental group 10 (100° C., 30 minutes) showing the highest CBN yield in Tables 1 and 2. As a result, when sulfuric acid, camphorsulfonic acid (CSA), and methanesulfonic acid (MSA) were used, the CBN content was 7.8%, 52.4%, and 20.0%, respectively. The yield was lower than that of PTSA, but CBN was produced. According to the results, when the same experiment was performed by varying the equivalent weight of PTSA showing the highest yield to 10 equivalent weights, 30 equivalent weights, and 40 equivalent weights, the yield was decreased to 52.3% when 10 equivalent weights of PTSA was used, but there was little change when 20 equivalent weights to 40 equivalent weights of PTSA were used.

Further, the results of calculating the contents of CBD, $\Delta^9$-THC, and CBN in UPLC chromatograms obtained by continuous microwave processing of the cannabis extract B including both CBD and $\Delta^9$-THC are summarized in Table 4.

TABLE 4

| Item | Temperature (° C.)-time (min) | Acid-equivalent weight (eq) | CBD (mg) | $\Delta^9$-THC (mg) | CBN (mg) | CBN yield* (%) |
|---|---|---|---|---|---|---|
| Extract B | — | | 52.3 | 84.9 | n.d | 0 |
| Experimental group 22 | 80-10 | PTSA-20 | n.d | 14.8 | 96.6 | 71.3 |
| Experimental group 23 | 80-20 | PTSA-20 | n.d | 7.7 | 98.1 | 72.4 |
| Experimental group 24 | 80-30 | PTSA-20 | n.d | 6.8 | 93.4 | 69.0 |

*CBN yield=(CBN mg/135.44 mg(Theoretical CBN amount at 100% conversion)×100**n.d=not detected Table 4 shows CBD, $\Delta^9$-THC, and CBN contents expressed in mg per 1 g of the extract, after dissolving the extract B of dry cannabis leaves in ethanol at a concentration of 200 ppm, adding 20 equivalent weights of PTSA, relative to CBD, and processing by continuous microwave irradiation at 80° C. for 10 minutes, 20 minutes, and 30 minutes. As a result, conversion of CBD and $\Delta^9$-THC to CBN was 71.3%, 72.4% and 69.0%, respectively.

Further, the results of calculating the contents of CBD, $\Delta^9$-THC, and CBN in UPLC chromatograms obtained by continuous microwave processing of the cannabis extract C including only $\Delta^9$-THC are summarized in Table 5.

TABLE 5

| Item | Temperature (° C.)-time (min) | Acid-equivalent weight (eq) | CBD (mg) | $\Delta^9$-THC (mg) | CBN (mg) | CBN yield* (%) |
|---|---|---|---|---|---|---|
| Extract C | — | | n.d | 71.1 mg | n.d | 0% |
| Experimental group 25 | 80-10 | PTSA-20 | n.d | 15.7 mg | 50.9 mg | 71.5% |
| Experimental group 26 | 80-20 | PTSA-20 | n.d | 5.3 mg | 61.2 mg | 86.0% |
| Experimental group 27 | 80-30 | PTSA-20 | n.d | 3.0 mg | 58.2 mg | 81.9% |

*CBN yield=(CBN mg/135.44 mg(Theoretical CBN amount at 100% conversion)×100**n.d=not detected Table 5 shows CBD, $\Delta^9$-THC, and CBN contents expressed in mg per 1 g of the extract, after dissolving the extract C in ethanol at a concentration of 200 ppm, adding 20 equivalent weights of PTSA, relative to $\Delta^9$-THC, and processing by continuous microwave irradiation at 80° C. for 10 minutes, 20 minutes, and 30 minutes. As a result, as shown in Table 5, conversion of $\Delta^9$-THC to CBN was 71.5%, 86.0%, and 81.9%, respectively.

Therefore, according to the above method, only $\Delta^9$-THC was produced through the cyclization reaction of CBD under the batch-type microwave conditions, but production of CBN through aromatization was not found. Meanwhile, it was found that CBD was converted to CBN via $\Delta^9$-THC under the continuous microwave conditions, and thus a method capable of mass-producing a processed product with a high content of CBN was developed.

As a result of the above experiments, when the cannabis leaf extracts A, B, and C were processed by the continuous microwave method, CBD or $\Delta^9$-THC which is the main cannabinoid component of cannabis, were efficiently converted into CBN. In detail, it was possible to obtain a continuous microwave-processed product, in which the major cannabinoid CBD and Δ9-THC complex components of cannabis were converted to the trace cannabinoid CBN with a conversion rate of 5.4% to 86.0%.

According to the method of producing cannabinoids according to an aspect, one or more of THC and CBN may be efficiently produced.

The composition according to another aspect may be used for anti-epilepsy, neuroprotection, vasorelaxation, anti-cancer, anti-inflammation, anti-diabetes, anti-bacteria, analgesia, anti-osteoporosis, immune enhancement, or antiemetic action, health functional foods, or cosmetics.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of producing cannabinoids, the method comprising irradiating microwaves to a reaction mixture comprising a *Cannabis* sp. plant or an extract thereof, an acid, and a solvent in a reaction vessel, wherein the microwave irradiation is carried out while flowing the reaction mixture from an inlet of the reaction vessel and out through an outlet of the reaction vessel,
wherein the *Cannabis* sp. plant or the extract thereof comprises one or more of CBD and THC, and the cannabinoid is one or more of THC and CBN,
wherein the reaction vessel is connected to a temperature control chamber for controlling the temperature inside the reaction vessel,
wherein the reaction vessel is contained in the temperature control chamber filled with a liquid to control a temperature of the reaction mixture,
wherein the temperature control chamber comprises a microwave-transparent material, and
wherein the acid is methanesulfonic acid (MSA), benzenesulfonic acid, naphthalenesulfonic acid, toluenesulfonic acid, para-toluenesulfonic acid (p-toluensulfonic acid, PTSA), camphor-10-sulfonic acid (CSA), or a mixture thereof.

2. The method of claim 1, further comprising isolating cannabinoids from the microwave-irradiated reaction mixture.

3. The method of claim 1, wherein the extract is obtained by a method comprising contacting the *Cannabis* sp. plant with one or more of water, a protonic solvent, an aprotonic solvent, and a mixture thereof.

4. The method of claim 1, wherein the *Cannabis* sp. plant comprises leaves, flower buds, seeds, nuts, trichomes, flower bracts, stems, or any part comprising cannabinoids.

5. The method of claim 1, wherein the content of one or more of CBD and THC in the extract is 1% by weight or more, based on the total weight of the extract.

6. The method of claim 1, wherein the microwave irradiation is carried out at 60° C. to 150° C.

7. The method of claim 1, wherein the microwave irradiation is carried out for a time sufficient to convert one or more of CBD and THC into one or more of THC and CBN.

8. The method of claim 1, wherein the microwave irradiation is carried out for about 5 minutes to about 180 minutes in a continuous reactor.

9. The method of claim 1, wherein the microwave irradiation is carried out under pressure.

10. The method of claim 1, wherein the microwave irradiation is carried out at a pressure of 2 atm to 100 atm.

11. The method of claim 1, wherein the microwave irradiation is carried out at a frequency of 300 MHz to 300 GHz.

12. The method of claim 1, wherein the microwave irradiation is carried out at a power of 3 W to 6 kW.

13. The method of claim 1, wherein, in the microwave irradiation, the solvent is water, C1-C12 alcohol, or an aqueous solution thereof.

14. The method of claim 1, wherein the solvent is ethanol, isopropanol, butanol, or a 50% to 99% ethanol aqueous solution.

15. The method of claim 2, wherein the isolated cannabinoids comprise 5% by weight to 100% by weight of CBN, based on the total weight of the isolate.

16. The method of claim 1, wherein the reaction vessel comprises a tube between the inlet of the vessel and the outlet of the vessel.

17. The method of claim 1, wherein the reaction vessel is made of a microwave-transparent material.

* * * * *